United States Patent
Walsh et al.

(10) Patent No.: US 10,522,326 B2
(45) Date of Patent: Dec. 31, 2019

(54) SYSTEMS AND METHODS FOR AUTOMATED MICROSCOPY

(71) Applicant: Massachusetts Institute of Technology, Cambridge, MA (US)

(72) Inventors: Michael Patrick Walsh, Somerville, MA (US); Dirk Robert Englund, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/896,377

(22) Filed: Feb. 14, 2018

(65) Prior Publication Data

US 2018/0233323 A1   Aug. 16, 2018

Related U.S. Application Data

(60) Provisional application No. 62/458,653, filed on Feb. 14, 2017.

(51) Int. Cl.
*H01J 37/302* (2006.01)
*H01L 27/146* (2006.01)
(Continued)

(52) U.S. Cl.
CPC .............. *H01J 37/28* (2013.01); *G01N 21/00* (2013.01); *G02B 21/00* (2013.01); *H01J 37/222* (2013.01);
(Continued)

(58) Field of Classification Search
CPC ...... H01J 37/222; H01J 37/28; H01J 37/3023; G02B 21/26; G02B 21/367; G02B 21/365;
(Continued)

(56) References Cited

U.S. PATENT DOCUMENTS 6,052,844 A * 4/2000 Walsh ................. A61H 33/02
 4/541.1
6,577,249 B1 * 6/2003 Akatsuka ............. G06K 9/3216
 340/988

(Continued)

OTHER PUBLICATIONS

Riedrich-Möller et al., "Deterministic Coupling of a Single Silicon-Vacancy Color Center to a Photonic Crystal Cavity in Diamond." Nano Letters 2014 14 (9), 5281-5287.

(Continued)

*Primary Examiner* — Wyatt A Stoffa
(74) *Attorney, Agent, or Firm* — Smith Baluch LLP

(57) ABSTRACT

A method of locating a substrate within a field of view of an imaging system includes acquiring an image of a first marker on a substrate in the field of view. The first marker has a first spatial pattern representing a position of the first marker relative to the substrate. The method also includes determining possible positions of the substrate based on the first spatial pattern and moving the substrate relative to the field of view based on the possible positions of the substrate. The method also includes acquiring an image of a second marker on the substrate in the field of view. The second marker has a second pattern representing a position of the second marker relative to the substrate. The method further includes determining the position of the substrate relative to the field of view based on the position of the second marker on the substrate.

26 Claims, 19 Drawing Sheets

(51) Int. Cl.
*H01J 37/28* (2006.01)
*H01J 37/22* (2006.01)
*G01N 21/00* (2006.01)
*G02B 21/00* (2006.01)
*H01L 21/68* (2006.01)
*H01L 23/544* (2006.01)

(52) U.S. Cl.
CPC .......... *H01J 37/3023* (2013.01); *H01L 21/68* (2013.01); *H01L 23/544* (2013.01)

(58) Field of Classification Search
CPC .................. G02R 31/2891; G06T 7/73; G06T 2207/10056; G06T 2207/30204; G03F 9/7003; G03F 9/7011; G03F 9/7084; G03F 9/7092; H01L 21/68; H01L 21/68764; H01L 23/544
USPC ..... 250/208.1, 526, 269.1, 330, 332, 370.08
See application file for complete search history.

(56) References Cited

U.S. PATENT DOCUMENTS

| | | | |
|---|---|---|---|
| 6,861,269 B2 * | 3/2005 | Kawai | G05B 19/4183 438/14 |
| 7,388,213 B2 * | 6/2008 | Sullivan | G01N 23/04 250/491.1 |
| 7,417,210 B2 * | 8/2008 | Ax, Jr. | G01C 11/025 250/201.1 |
| 7,424,174 B2 * | 9/2008 | Furuhashi | G06T 7/55 382/190 |
| 7,535,581 B2 * | 5/2009 | Moon | B82Y 10/00 356/501 |
| 7,538,564 B2 * | 5/2009 | Ehrmann | G01R 31/2891 324/754.03 |
| 7,838,858 B2 * | 11/2010 | Okita | G03F 9/7003 250/221 |
| 7,918,404 B2 * | 4/2011 | Lapstun | G06K 7/14 235/462.04 |
| 8,413,027 B2 * | 4/2013 | Lapstun | G06F 3/0321 178/18.01 |
| 8,450,674 B2 * | 5/2013 | Yang | A61B 5/0059 250/208.1 |
| 8,737,609 B1 * | 5/2014 | Durst | G06K 19/086 380/54 |
| 8,811,715 B2 * | 8/2014 | McGarry | G06T 7/0004 348/125 |
| 9,792,688 B2 * | 10/2017 | Nasu | G06K 9/03 |
| 10,078,269 B2 * | 9/2018 | Goodwin | G03F 7/70141 |
| 10,134,133 B2 * | 11/2018 | Zhao | G01D 1/00 |
| 2002/0053634 A1 * | 5/2002 | Watanabe | B82Y 10/00 250/201.2 |
| 2004/0167806 A1 | 8/2004 | Eichhorn et al. | |
| 2004/0233461 A1 * | 11/2004 | Armstrong | G01C 11/025 356/620 |
| 2004/0257573 A1 * | 12/2004 | Matsumoto | G03F 9/7046 356/401 |
| 2007/0096763 A1 * | 5/2007 | Ehrmann | G01R 31/2891 324/750.23 |
| 2007/0188758 A1 * | 8/2007 | Matsumoto | G03F 9/7046 356/401 |
| 2008/0001066 A1 * | 1/2008 | Ax | G01C 11/025 250/208.1 |
| 2009/0195786 A1 | 8/2009 | Gastaldo | |
| 2010/0259741 A1 * | 10/2010 | Koga | G03F 9/7011 355/67 |
| 2011/0058151 A1 * | 3/2011 | Takenaka | G03F 9/7011 355/53 |
| 2011/0108707 A1 * | 5/2011 | Cui | A61B 5/0059 250/208.1 |
| 2014/0212909 A1 * | 7/2014 | Tambe | G06T 7/246 435/29 |
| 2016/0085062 A1 * | 3/2016 | Kalkbrenner | G02B 21/006 348/49 |
| 2016/0103178 A1 * | 4/2016 | Zeise | G01R 31/2891 324/750.23 |
| 2016/0231553 A1 * | 8/2016 | Piestun | G02B 21/367 |
| 2018/0088048 A1 | 3/2018 | Dong et al. | |
| 2018/0098468 A1 * | 4/2018 | Takama | H05K 13/08 |
| 2018/0113084 A1 * | 4/2018 | Hench | G01N 23/20083 |
| 2018/0114335 A1 * | 4/2018 | Houri | G06K 9/00671 |
| 2018/0151400 A1 * | 5/2018 | Wang | H01L 21/68 |
| 2018/0275535 A1 * | 9/2018 | Fujishima | G03F 7/70216 |

OTHER PUBLICATIONS

Liu et al., Cryogenic photoluminescence imaging system for nanoscale positioning of single quantum emitters. Rev Sci Instrum. Feb. 2017;88(2):023116. doi: 10.1063/1.4976578.

Li et al., Coherent spin control of a nanocavity-enhanced qubit in diamond. Nat. Commun. 6:6173 doi: 10.1038/ncomms7173 (2015).

Schröder et al., Scalable focused ion beam creation of nearly lifetime-limited singlequantum emitters in diamond nanostructures. Nat Commun. May 26, 2017;8:15376. doi:10.1038/ncomms15376.

International Search Report and Written Opinion in International Patent Application No. PCT/US2018/018180 dated Apr. 30, 2018, 8 pages.

Wang et al., 3D super-resolution imaging with blinking quantum dots. Nano Lett. Nov. 13, 2013; 13(11):5233-41. doi:10.1021/nl4026665. Epub Oct. 10, 2013.

\* cited by examiner

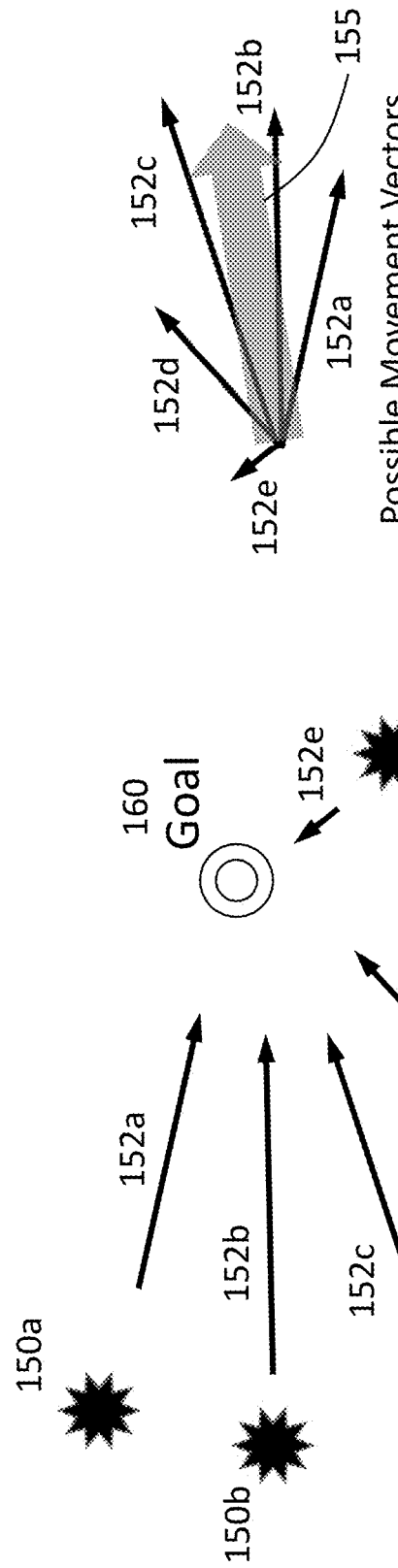

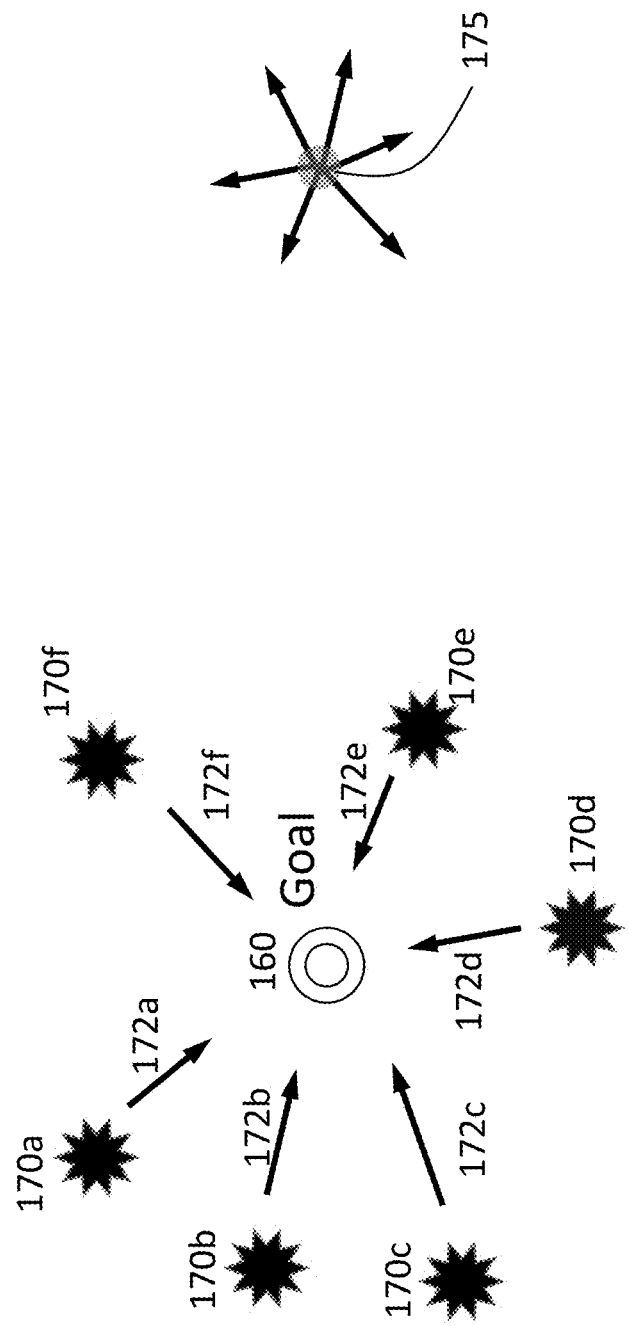

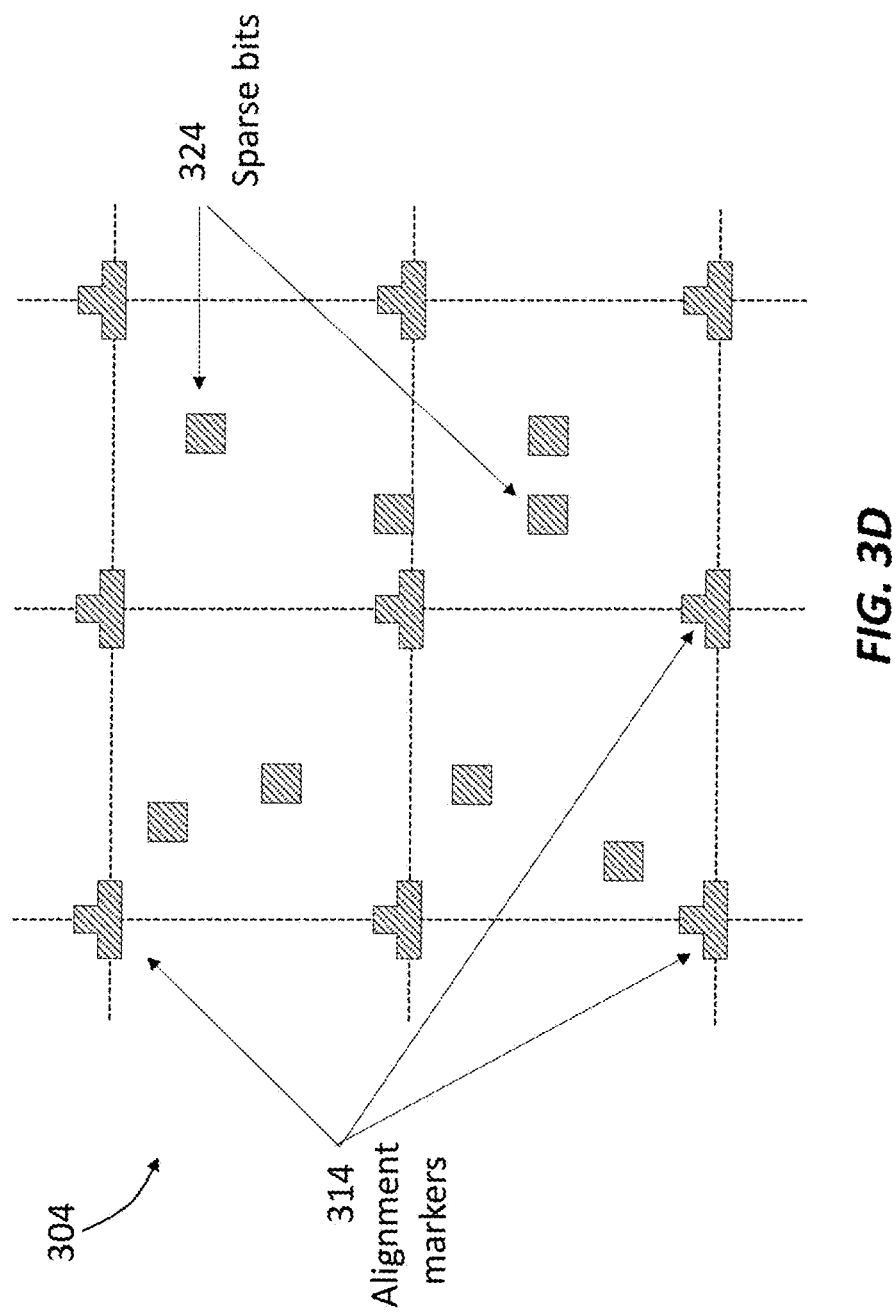

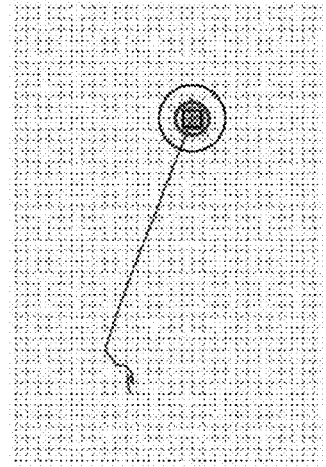
FIG. 7A  
3 bits (quite repetitive)
FIG. 7B  
4 bits
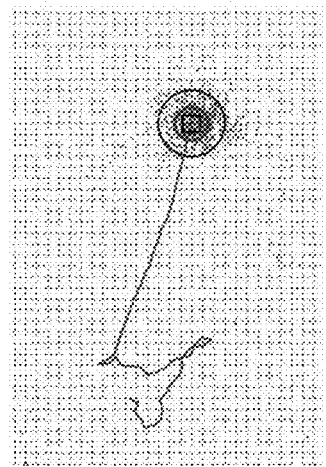
FIG. 7C  
6 bits
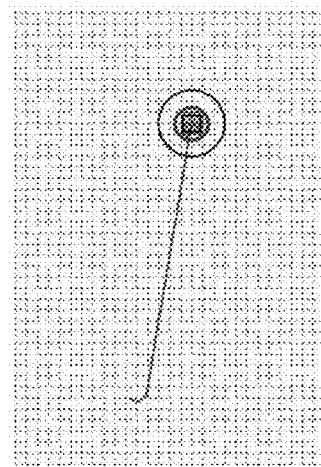
FIG. 7D  
Infinite bits — (perfectly unique)

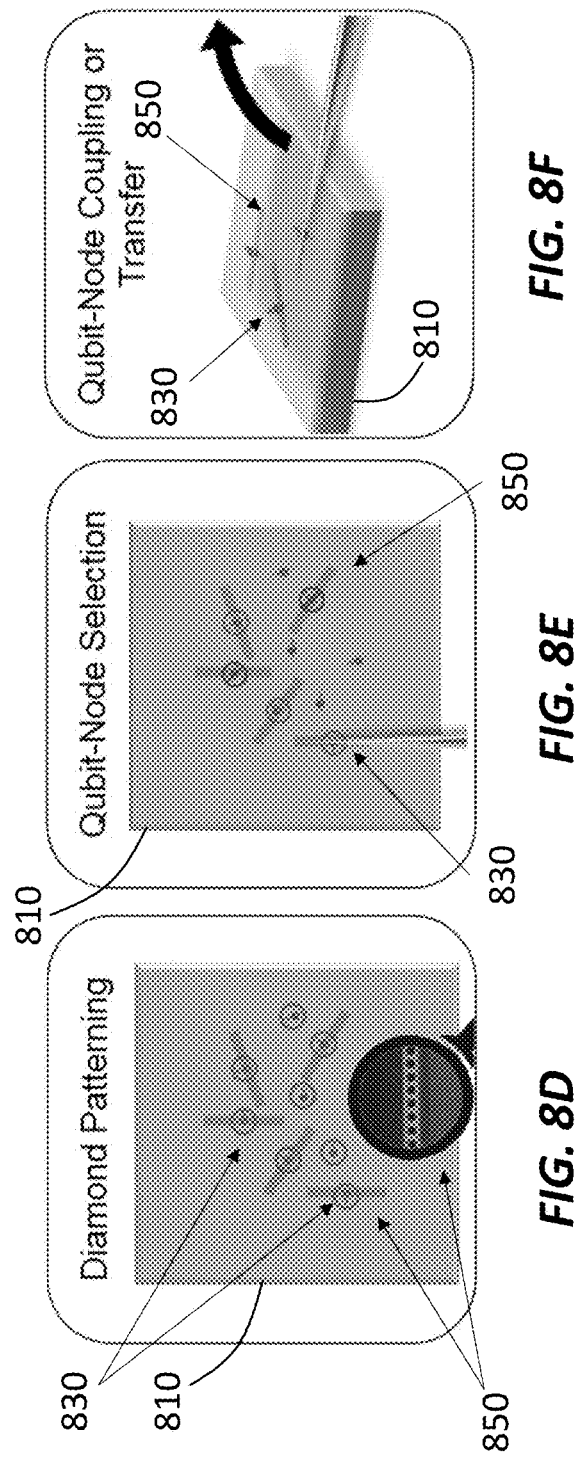

SYSTEMS AND METHODS FOR AUTOMATED MICROSCOPY

CROSS-REFERENCE TO RELATED APPLICATIONS

This application claims the priority benefit, under 35 U.S.C. § 119(e), of U.S. Provisional Patent Application No. 62/458,653, filed on Feb. 14, 2017, and entitled "MACHINE-VISION GUIDED MICROSCOPY FOR AUTONOMOUS CHARACTERIZATION OF QUANTUM EMITTERS AND PHOTONIC NANOSTRUCTURES." This application is incorporated herein by reference in its entirety.

GOVERNMENT SUPPORT

This invention was made with Government support under Grant No. DMR-1231319 awarded by the National Science Foundation, and Grant No. W911NF-15-2-0067 awarded by the Army Research Office. The Government has certain rights in the invention.

BACKGROUND

Quantum emitters, such as color centers (e.g., nitrogen-vacancy color centers in diamond) and epitaxial quantum dots (QDs), have a wide range of applications in quantum information processing (QIP), bio-imaging, and quantum-sensing. For example, QDs produced by Stranski-Krastanov self-assembled growth can be used in single-photon sources having nearly transform-limited emission linewidths. Currently, most quantum emitters are randomly positioned, such as naturally occurring impurity centers or self-assembled QDs, due to the high optical quality of such structures.

Nanophotonic structures, such as gratings, waveguides, and micro-cavities, are usually fabricated around or near the quantum emitters in order to construct practical devices. Since these quantum emitters are usually randomly distributed on a substrate, the fabrication of the nanophotonic structures usually involves locating the spatial position of these quantum emitters, or creating a large number of structures and relying on probability to successfully align to an emitter. Existing methods to locate quantum emitters include atomic force microscopy, scanning confocal microscopy, and scanning electron microscopy. However, these methods are usually manual and therefore can be time consuming.

SUMMARY

Embodiments of the present technology generally relate to automated microscopy. In one example, a method of locating a substrate within a field of view of an imaging system includes acquiring, with the imaging system, an image of a first marker on a substrate in the field of view. The first marker has a first spatial pattern representing a position of the first marker relative to the substrate. The method also includes determining a plurality of possible positions of the substrate relative to the field of view based on the first spatial pattern and moving the substrate relative to the field of view based on the plurality of possible positions of the substrate relative to the field of view. The method also includes acquiring, with the imaging system, an image of a second marker on the substrate in the field of view. The second marker has a second pattern representing a position of the second marker relative to the substrate. The method further includes determining the position of the substrate relative to the field of view based on the position of the second marker on the substrate.

In another example, an imaging system includes an image sensor to acquire an image of a first marker on a substrate in the field of view. The first marker has a first spatial pattern representing a position of the first marker relative to the substrate. The imaging system also includes a processor, operably coupled to the image sensor, to determine at least one possible position of the substrate relative to the field of view based on the first spatial pattern. A translation stage is operably coupled to the processor to move the substrate relative to the field of view based on the at least one possible position of the substrate relative to the field of view.

In yet another example, a method of locating a substrate within a field of view of an imaging system includes acquiring, with the imaging system, an image of a first marker on a substrate in the field of view. The first marker having a first unique spatial pattern encoding a position of the first marker relative to the substrate and a checksum. The method also includes determining at least one possible position of the substrate relative to the field of view based on the position of the first marker relative to the substrate and the checksum.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 1B-1E illustrate selection of movement directions that can be used in the system shown in FIG. 1A.

FIG. 3D shows a schematic of a marker using sparse encoding.

FIGS. 7A-7D show motion traces of an instrument toward a goal position with 3 bits, 4 bits, 6 bits, and an infinite (perfectly unique) number of bits, respectively, encoded in the markers.

FIGS. 8A-8F illustrate a method of fabricating photonic structures around defect centers in a diamond substrate using automated microscopy techniques.

DETAILED DESCRIPTION

Systems for Automated Microscopy Using Encoded Markers

To address the drawbacks in existing methods of locating nanostructures (e.g. quantum emitters), systems and methods described herein employ a scalable architecture for automated microscopy. This approach takes advantage of markers that encode information about the spatial location of the marker on a sample (e.g., a substrate). Based on these markers, a compound machine vision-Bayesian inference system can be implemented to allow the microscope to navigate and map samples. Using a user-defined database scheme, the microscope can make data available in a real-time manner, register all identified locations, and use sample records to revisit known locations.

In addition, methods described herein can be implemented by a computer via processor-executable instructions (computer code) in an automated mode. The computer code can have a modular architecture that can make it easy to design and perform a variety of experiments with arbitrary hardware at any or all locations on the sample. Leveraging various levels of abstraction, a user can operate with a plug-and-play mentality or choose to design complex experiments that easily plug into the autonomous architecture. Given a shared database, multiple hardware realizations of the microscope can navigate to predefined locations for an extended set of measurements.

The automated microscopy described herein has at least two advantages over existing methods of locating nanostructures. First, the markers are encoded with location information with respect to the sample, thereby allowing fast acquisition of location information upon imaging and decoding the markers. Second, the automated microscopy allows automated characterization of many fields of view as the microscopy navigates across the sample. This navigation can register a significant number of emitters (e.g., on the order of millions) into a database that can be used in subsequence processing (e.g., fabrication of nanophotonic devices around or nearby the emitters). The addition of electron beam lithography (EBL) markers further allows fabrication on a larger scale that can be done with local alignment of a focused ion beam (FIB) machine.

Figure 1A:
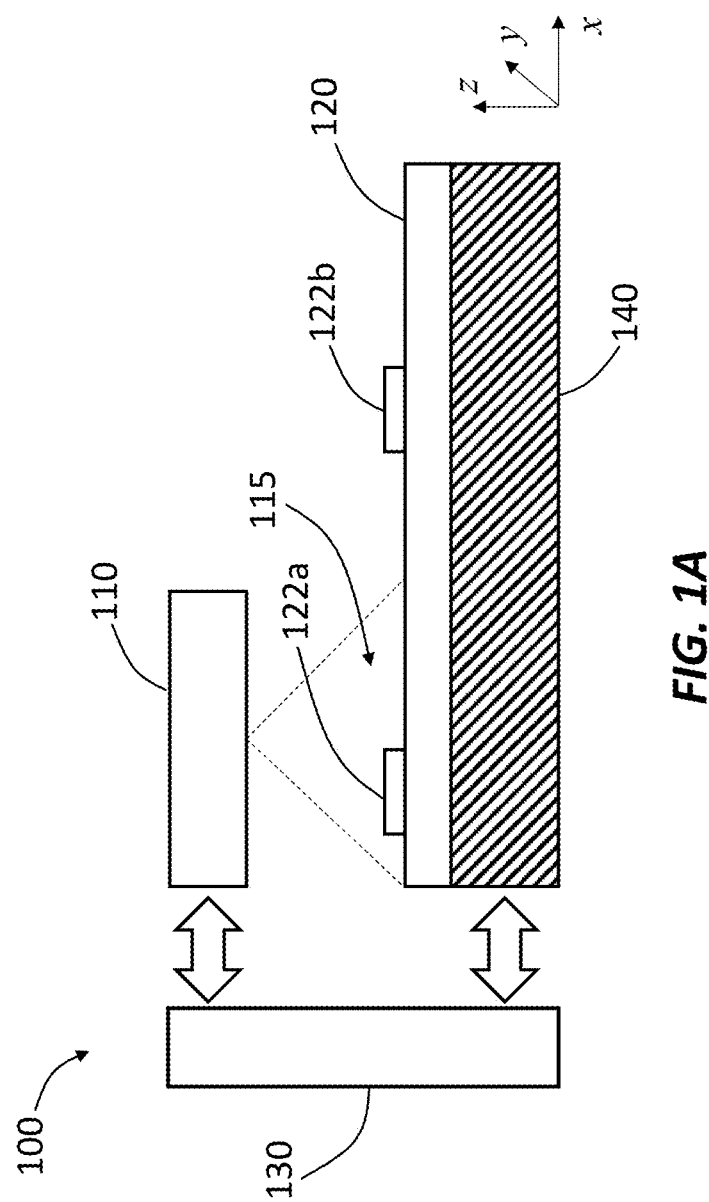
FIG. 1A shows a schematic of a system for automated microscopy using markers patterned with location information.

FIG. 1A shows a schematic of a system 100 for automated microscopy using markers patterned with location information (also referred to as position information). The system 100 includes an image sensor 110 having a field of view 115 to acquire an image of a first marker 122a disposed on a substrate 120 (also referred to as a sample 120). The first maker 122a is within the field of view 115 and has a spatial pattern representing the position of the first marker 122a relative to the substrate 120. The system 100 also includes a processor 130, operably coupled to the image sensor 110, to read the image of the first marker 122a acquired by the image sensor 110 and decode the spatial pattern of the first marker 122a so as to determine at least one possible position of the substrate 120 relative to the field of view 115. In one example, the first marker 122a is a unique marker and encoded with sufficient information for the processor 130 to determine the location of the first marker 122a. For example, the first marker 122a can be encoded with the row and column numbers on the substrate 120. In another example, the first marker 122a can be a non-unique marker, in which case the processor 130 determines the location of the substrate 120 (or the location of the first marker 122a) based on the spatial pattern of the first marker 122a and some additional information, such as the spatial pattern of another marker 122b (more details of unique and non-unique markers are provided below).

A translation stage 140 is operably coupled to the processor 130 to move the substrate 120 relative to the field of view 115. In one example, the translation stage 140 is mechanically coupled to the substrate 120 to move the substrate 120. In another example, the translation stage 140 is configured to move the imager sensor 110 so as to cause the field of view 115 to cover another section of the substrate 120. The processor 130 is configured to control the operation of the translation stage 140 based on the possible position of the substrate 120 determined via the first marker 122a. For example, in the event that the first marker 122a is a non-unique marker, the processor 130 can control the translation stage 140 to move the substrate 120 (or the imager sensor 110) so as to capture the second marker 122b in the field of view 115. The processor 130 can then determine the position of the substrate 120 based on the combination of information encoded in the two markers 122a and 122b.

In another example, the processor 130 can control the translation stage 140 to move the field of view 115 to a target location. For example, the system 100 may identify a quantum emitter in previous navigation and register the location of the quantum emitter. The processor 130 can then control the translation stage 140 to move the field of view 115 to the identified quantum emitter so as to facilitate the fabrication of nanophotonic devices nearby the quantum emitter. In this instance, the processor 130 can determine the current location of the field of view 115 and calculate the distance and direction between the current location and the target location, followed by controlling the translation stage 140 to move the field of view 115 toward the target location based on the calculated distance and direction.

The translation stage 140 can move the field of view 115 laterally (i.e., along the x and y directions as illustrated in FIG. 1A), vertically (i.e., along the z direction as illustrated in FIG. 1A) or vertically and laterally. In this instance, the translation stage 140 can change the focus of the image sensor 110 so as to capture a sharp image of the first marker 122a (and/or the second marker 122b).

The image sensor 110 in the system 100 can include any appropriate detectors, such as a charge-coupled device (CCD), a complementary metal-oxide-semiconductor (CMOS) sensor, or a photodiode, among others. The image sensor 110 can include one or more imaging optics (e.g., imaging lenses) to facilitate the acquisition of the images. The image sensor 110 may also be part of a confocal imaging system.

The system 100 uses the first marker 122a and the second marker 122b (collectively referred to as markers 122) across the substrate 120 to determine their locations on the substrate 120. In one example, the markers 122 can include a one-dimensional bar code. In another example, the markers 122 can include a custom version of Quick Response (QR) codes, which is a 2-dimensional array of information (e.g. digital bits). The markers 122 can satisfy two conditions to facilitate the operation of the system 100. First, the markers 122 are encoded with location information that can be recognized by the processor 130 (e.g., the locations of the markers 122 are known). Second, each marker 122a and 122b can fit within the field of view 115 of the imager sensor 110. The specific geometry and layout of the markers 122 can be defined by the user or the application (examples of markers 122 are described below with reference to FIGS. 2-3D).

In one example, the markers 122a and 122b (collectively referred to as markers 122) can be directly fabricated on or in the substrate 120 via, for example, optical or electron beam lithography techniques. In another example, the markers 122 can be fabricated on a transparent substrate (e.g., a glass slide), which is disposed on the substrate 120. In this instance, the sample 120 can include biological tissue (e.g., a tumor sample) for investigation.

Although FIG. 1A shows only two markers 122 disposed on the substrate 120, in practice, the system 100 can include multiple markers distributed on the substrate 120. For example, the system 100 can include a two-dimensional (2D) array of markers to form a coordinate system to mark locations on the substrate. In one example, each marker is unique such that decoding one marker can yield sufficient information to determine the location of that marker. For example, the pattern of each marker and the corresponding location of that marker is stored in a database. Upon receiving the image of the marker, the processor 130 can compare the acquired image with stored patterns in the database to find a matching pattern and determine that this corresponding location of the matching pattern is the location of the marker. Alternatively or additionally, each marker can be encoded with the location information in the QR code. For example, the encoded information can be the 2D coordinates (e.g., row number and column number) of the marker.

In another example, the markers 122 are non-unique and the location of each marker (accordingly the relative location of the substrate 120 with respect to the field of view 115) can be determined based on information encoded in more than one marker. For example, the system 100 can include a 2D array of markers, in which one row of markers is encoded with only the row number, while adjacent rows of markers are encoded with the column number. In this instance, the translation stage 140 can move the field of view 115 to capture one marker to acquire the row number and then move the field of view 115 to capture another marker nearby the first marker to acquire the column number. The combination of information from the two markers can therefore allow the processor 130 to determine the location of each marker.

In yet another example, the processor 130 can determine a first group of possible locations based on the first marker 122a and determine a second group of possible locations based on the second marker 122b. The processor 130 can then determine the overlapping between the first group of locations and the second group of locations. If there is only one overlapped location, the processor 130 can determine that the overlapped location is the location (or approximate location) of the two markers (given that they are close to each other). If there are several overlapped locations, the processor 130 can control the translation stage 140 to move the field of view 115 to capture a third marker. This process can continue until the processor 130 determines a unique location.

The group of locations associated with a pair of nearby markers may not have any overlapping markers. In this instance, the processor 130 can determine the degree of proximity between locations in these two groups. If two locations from two groups are sufficiently close (e.g., the separation distance is below a threshold value), the processor 130 can determine that these two locations correspond to the two locations of the two markers.

In addition to position information, the markers 122 can also provide direction information for the translation stage 140 to move the field of view 115. For example, the processor 130 may be configured to move the field of view 115 to a target position $(x_0, y_0)$ where a quantum emitter was identified before. After acquiring the current position $(x_1, y_1)$, the processor 130 can determine a vector $(x_0-x_1, y_0-y_1)$ and then control the translation stage 140 to move the field of view 115 along this vector. In addition, as the field of view 115 is moving, the processor 130 can update this vector every time a new current position is determined.

When non-unique markers are used, each marker is associated with a group of possible positions. In this instance, the processor 130 can determine the movement direction based on the distances between each possible position and the target position. For example, at one marker, the possible positions include $(x_1, y_1), (x_2, y_2) \ldots (x_n, y_n)$, where n is an integer. The processor 130 can then determine the vectors (including distances and directions) associated with each possible position. The processor 130 can then choose the direction associated with the weighted average of the set of vectors distance toward the target position. The weight assigned to a given possible position depends on the belief (or likelihood) that the field of view 115 is at the given possible position. In the event that the weighted average vector is zero, the processor 130 can choose a random direction to move the field of view 115 and then determine the next step.

FIGS. 1B-1E illustrate the selection of the direction for the next move. FIG. 1B shows that the processor 130 determines possible positons 150a to 150e based on a given marker (e.g. first maker 122a or the second marker 122b). The processor 130 also calculates vectors 152a to 152e representing the path between the corresponding possible positions 150a to 150e and the goal position 160. FIG. 1C shows that the weighted average vector 155, which is the direction to be taken for the next movement. FIG. 1C shows the scenarios of zero weighted average vector, in which the processor 130 determines possible positions 170a to 170f and the associated vectors 172a to 172f toward the goal position 160. The weighted average vector 175 of these vectors 172a to 172f is zero, in which case the processor 130 can choose and random direction for next move.

Since the position of the field of view 115 (and accordingly the positions of the substrate 120 and the markers 122) is determined based on the information encoded in the markers 122, the resolution (or the precision of the determined position) of this technique can be finer than the precision of the translation stage 140 and/or the diffraction limit of the imager sensor 110. For example, the markers 122 can be fabricated using electron beam lithography (EBL) techniques, which can have a resolution of about 10 nm or finer (i.e. sub-10 nm resolution), which is much lower than the stage's precision and the markers. In this instance, the markers 122 can be imaged and localized with a position precision of about 10 nm. In general, the precision of the determined position can be about 50 nm or finer (e.g., about 50 nm, about 40 nm, about 30 nm, about 20 nm, about 10 nm, or finer, including any values and sub ranges in between).

Figure 2:
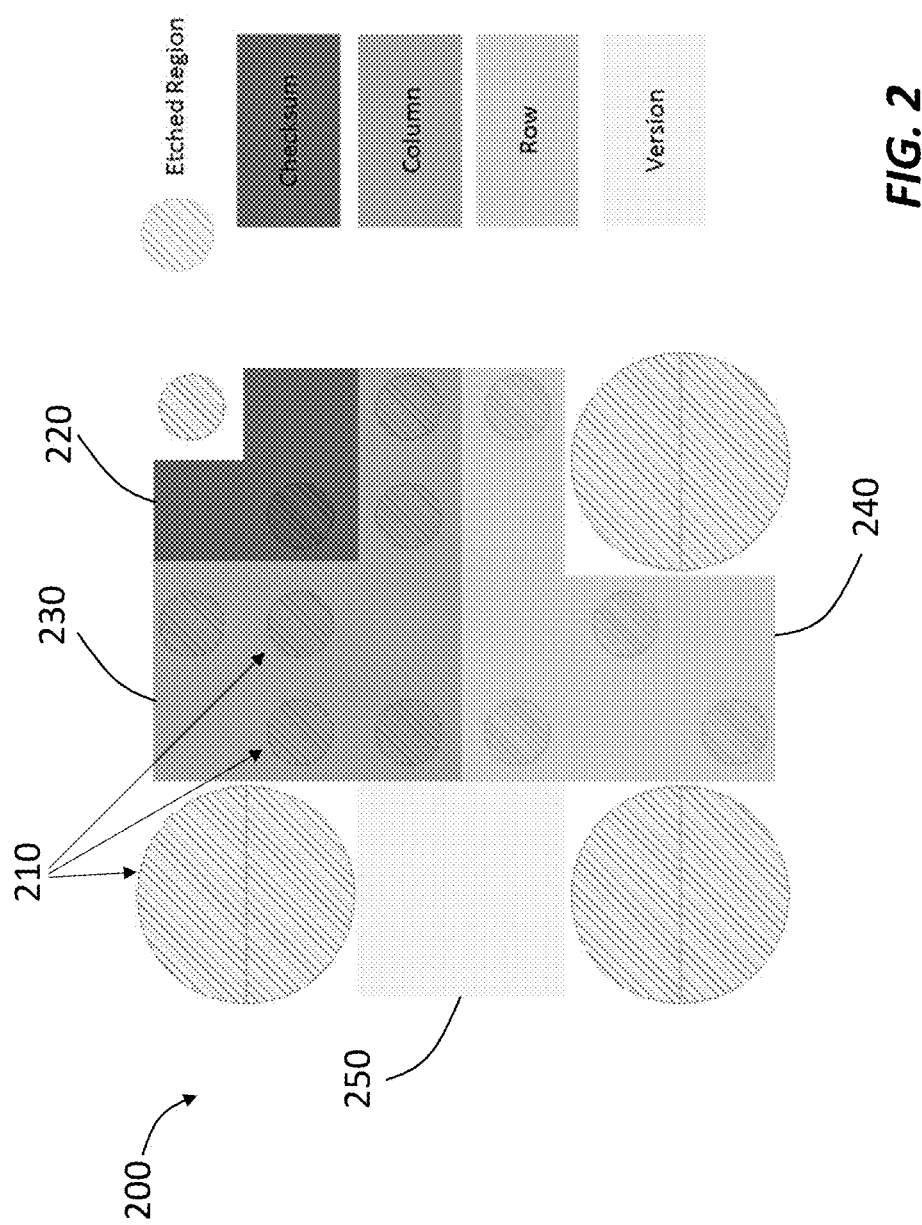
FIG. 2 shows a schematic of a marker that can be used in the system shown in FIG. 1A.

FIG. 2 shows a schematic of a marker 200 that can be used in the system 100. The layout pattern of the marker 200, formed by multiple etched areas 210, includes a square grid, indexed by row and column. The marker 200 uses 16 bits to encode the location (including 8 bits to encode the column number 230 and 8 bits to encode the row number 240), 4 bits to encode the version 250, 1 bit as a constant "pad", and 3 bits as a checksum 220. It is convenient to contain all relevant information in the marker 200 to calculate the position of the marker (e.g., the pitch between rows and/or columns). As such, the version bits 250 allow the user to define a set of different marker designs that have some flexibility in the location on the substrate (or chip). The version bits 250 also allows the user to define checksum and pad definitions (e.g. allowing customization of the encoded information) that the microscope can distinguish without user intervention. The pad is a constant bit that helps a processor (e.g., the processor 130) identify this pattern to be a marker once an image sensor (e.g., the image sensor 110) locates the three large circles on the corners. The geometry of the marker 200 has a small footprint with error-detection capability (summing bits mod 4 to assure that the resulting value equals the checksum; if not, the processor can determine that there is an error).

The format of the marker 200 can be relaxed to construct, for example, simpler markers. For example, all the available bits can be used to encode an integer as an identifier of the marker. In another example, most of the bits can be used to encode an integer and a few bits (e.g., 1 to 5 bits) can be reserved for error detection and correction (e.g. a simple checksum as described above to detect errors; or if more bits can be spared, a Reed-Solomon Code can be used to correct some number of bit flips). In these instances, a map can be formed to include the locations of each marker on the sample. Once the image sensor acquires the image of the marker and the processor reads the integer from the image, the processor can then compare the integer with the map to determine the location of the marker.

Figure 3C:
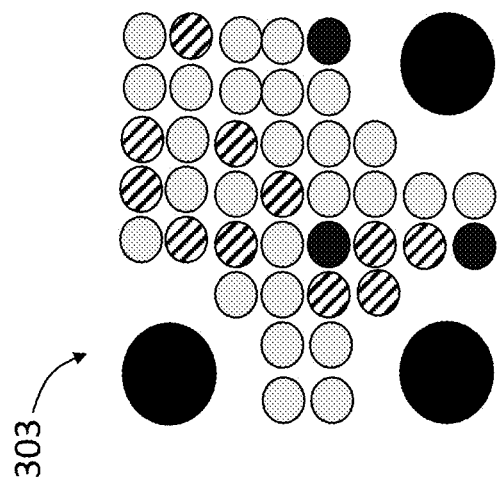
FIGS. 3A-3C show schematics of markers including 24 bits, 25 bits, and 40 bits of information, respectively.
Figure 3B:
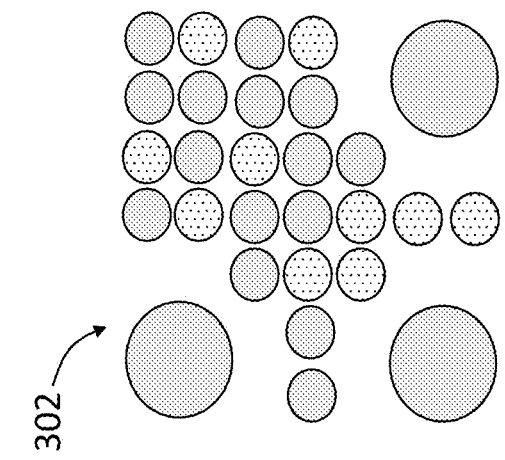
Figure 3A:
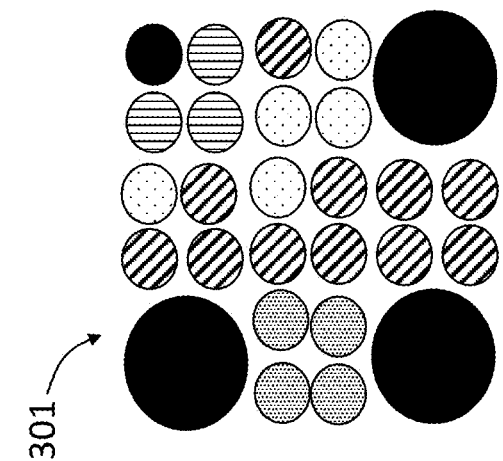

FIGS. 3A-3D show schematics of markers encoded with different bits of information. FIG. 3A shows a schematic of a marker 301 encoded with 24 bits of information, FIG. 3B shows a schematic of a marker 302 encoded with 25 bits of information, and FIG. 3C shows a schematic of a marker 303 encoded with 40 bits of information. In these markers 301 to 303, each bit of information is represented by a small circle (e.g., one etched area). In general, markers encoded with a greater number of bits also occupy a larger area on the sample. For extremely large samples, it might be helpful to use larger marker to include more spatial information. It might also be beneficial to use larger codes to reserve bits for error detection and correction when, for example, the fabrication is prone to imperfection. On the other hand, for samples where area is at a premium, it might be desirable to use smaller codes. Non-unique markers, which are usually smaller, can also be used. In this instance, the microscope can move around the sample to capture multiple markers before confidently defining the location of the field of view uniquely.

FIG. 3D shows a schematic of a marker 304 using sparse encoding. The marker 304 includes alignment markers 314 for determining orientation and sparse bits 324 that are encoded with information (e.g. location information, checksum, error-correction code, etc.). Sparse encodings convey information through placement of etched regions and have the advantage of covering a smaller total area of the field of view, despite that the bounds/extent of such a marker may extend into the full field of view. The sparse encoding etched regions can also be larger and fewer in number. As such, optical lithography may be used for an inexpensive fabrication process. The larger encodings also allow for use of such a design at multiple zoom levels. The marker 304 shown in FIG. 3D includes 64 possible positions per marker and two sparse bits per marker.

Aberration Correction of Marker Images

Referring back to FIG. 1A, the image sensor 110 in the system 100 might be subject to image distortion, primarily manifested in radial and tangential components. Radial distortion is caused primarily from the shape of the lens in the image sensor 110, i.e., rays entering the lens at different radii from the optical axis are focused to different locations. Tangential distortion is typically a result of lenses not being perfectly orthogonal to the optical axis.

Aberrations in the images acquired by the image sensor 110 can be corrected using an array of points (or any other shapes, such as circles, squares, and stars) having known locations and spanning the field of view 115. In one example, the array of points can be the markers themselves. In another example, the array of points can include additional points fabricated in the substrate 120. The processor 130 can apply corrections to the image to counteract aberrations introduced by lenses.

More specifically, a Brown-Conrady model can be used to account for radial and tangential distortion. In this approach, the field of view 115 navigates to an aberration-correction region where there is an array of patterned points. Equations (1)-(4) below can be used to select the vector $a=[a_1, a_2, \ldots a_5]$, such that the error between the true grid locations and the imaged grid locations is reduced or minimized:

$$\text{radial} = (1 + a_1 r^2 + a_2 r^4 + a_3 r^6) \cdot \hat{x} \quad (1)$$

$$\text{tangential}_x = 2a_4 xy + a_5 (r^2 2x^2) \quad (2)$$

$$\text{tangential}_y = a_4 (r^2 + 2y^2) + 2a_5 xy \quad (3)$$

$$\text{BrownConrady} = \text{radial} + \text{tangential} \quad (4)$$

with $\hat{x}=[x, y]$, $r^2=x^2+y^2$ and tangential=[tangential$_x$, tangential$_y$].

Figure 4A:
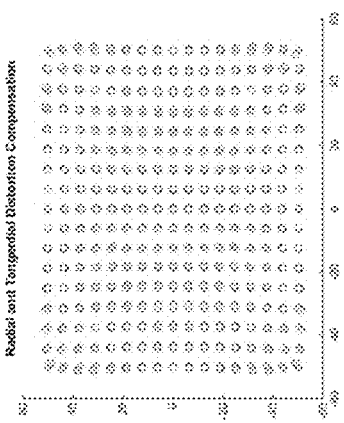
FIGS. 4A-4D illustrate aberration correction for images acquired in the system shown in FIG. 1A using the Brown-Conrady model.
Figure 4C:
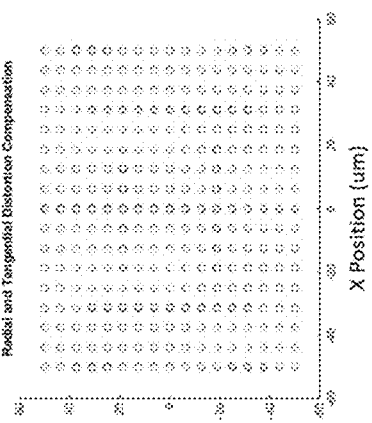
Figure 4B:
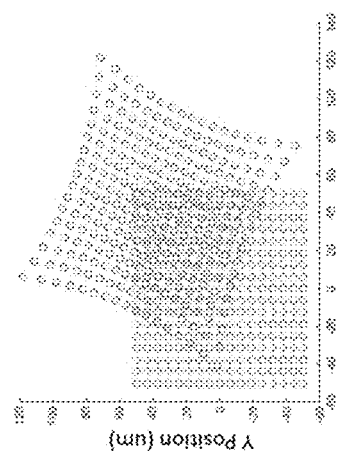
Figure 4D:
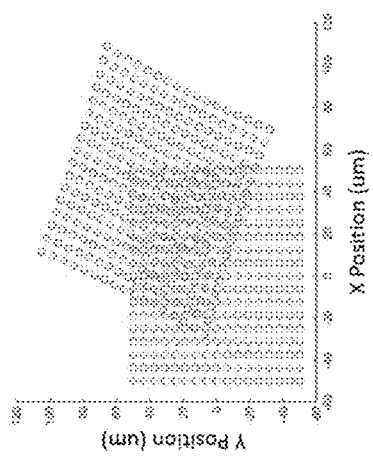

FIGS. 4A-4D illustrate aberration correction using the Brown-Conrady model. FIGS. 4A and 4B show images with significant and mild aberrations, respectively. FIGS. 4C and 4D show images after aberration correction. It can be seen that the aberration correction can compensate for both radial and tangential distortion.

Systems for Automated Microscopy Including Multiple Excitation Sources

The power and flexibility of the architecture described herein lies in its modularity that allows users to design experiments with a complex set of hardware. The resulting system is not limited to a single stage or single imaging system. Multiple excitation sources and multiple imaging systems can also be configured into the same automated microscopy system.

Figure 5:
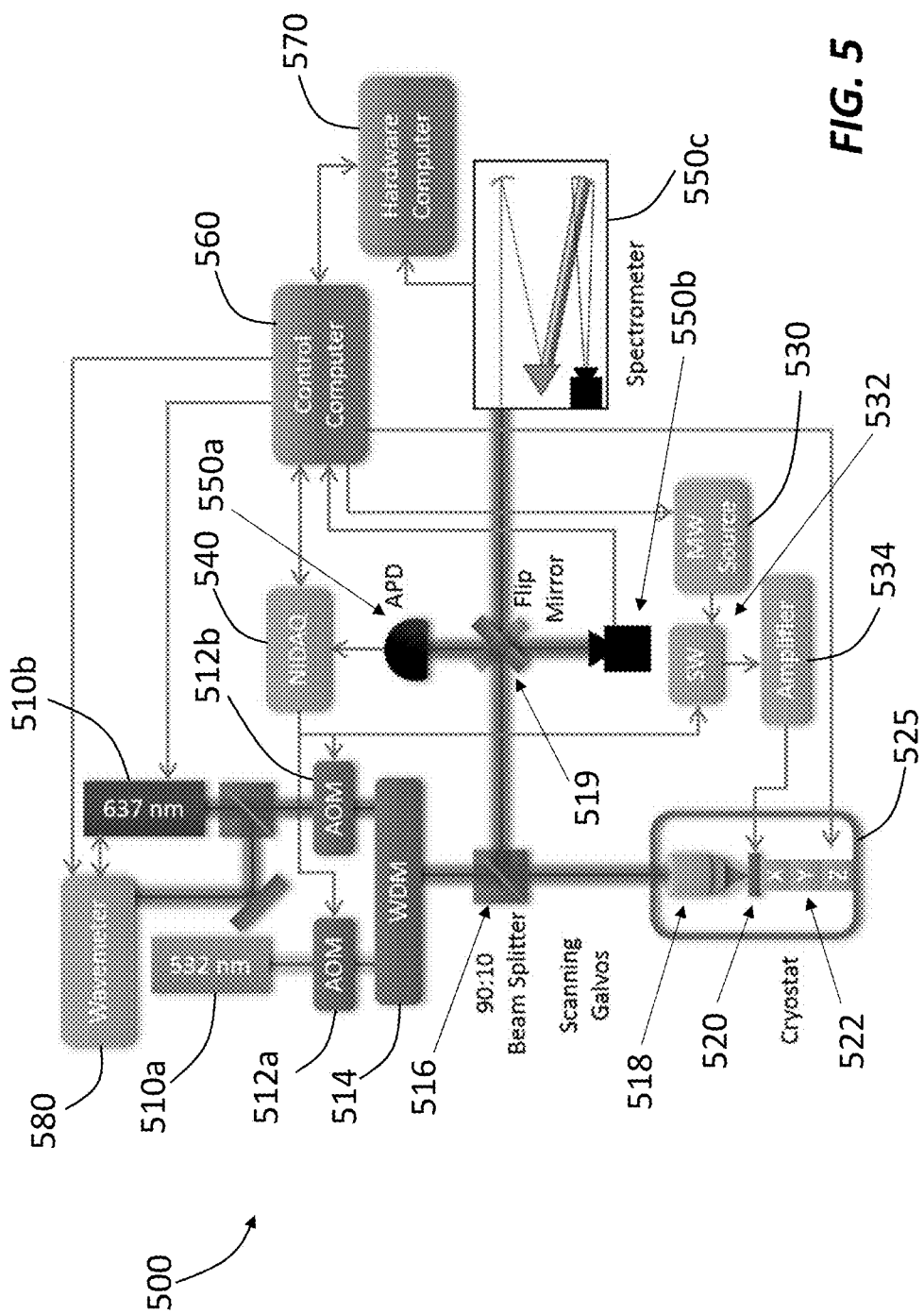
FIG. 5 shows a schematic of a system for automated microscopy using multiple excitation sources and multiple imaging systems.

FIG. 5 shows a schematic of a system 500 for automated microscopy using multiple excitation sources. The system 500 includes two laser sources 510a (e.g., operating at 532 nm) and 510b (e.g., operating at 637 nm). A wavemeter 580 is in optical communication with these two laser sources 510a and 510b to calibrate and/or adjust the operating wavelengths of the two laser sources 510a and 510b. The first laser source 510a is in optical communication with a first acousto-optic modulator (AOM) 512a and the second laser source 510b is in optical communication with a second AOM 512b. The two lasers sources 510a and 510b can be turned on/off by applying a digital signal to the corresponding AOM 512a and 512b, thereby modulating the excitation beams for pulsed measurements.

The excitation beams provided by the two laser sources 510a and 510b are multiplexed at a multiplexer 514 before being delivered to a sample 520 via a beam splitter 516. The sample 520 is disposed on a 3D translation stage 522 that can move the sample 520 along the x, y, and z directions. The translation stage 522 can include a stepper-motor and/or a piezoelectric stage. The imaging optics 518, the sample 520, and the translation stage 522 can be disposed in a chamber 525, such as a cryostat.

A microwave source 530 is used in the system 500 to apply a microwave to the sample 520 via a switch 532 and an amplifier 534. The switch 532 can also be used to gate the microwave source 530 in response to a digital signal, which can be programed into a National Instruments data acquisition (NIDAQ) device 540 for application of pulse sequences. The microwaves can be used, for example, to perform spin measurements on quantum devices.

The light reflected by the sample 520 can be delivered into three imaging systems via imaging optics 518 (e.g., a microscope) and a flip mirror 519. The first imaging system includes an avalanche-photo diode (APD) 550a that can be used to measure single photon sources. The second imaging system includes a camera 550b, such as a CCD camera, which can be used to image the field of view. The third imaging system includes a spectrometer 550c to measure spectra of emissions from the sample 520. A hardware computer 570 is used in the system 500 to process the data acquired by the spectrometer 550c and send the processed data to a control computer 560.

The control computer 560 controls the operation of the translation stage 522. For example, the control computer 560 can control the translation stage 522 to move the sample 520 toward a target position. Alternatively or additionally, the control computer 560 can control the translation stage 522 to move the sample 520 so as to allow the imaging optics 518 to capture multiple markers on the sample 520. The movement of the translation stage 522 can be based on signals provided by the three detectors 550a, 550b, and 550c. The control computer 560 is also operably coupled to the two AOMs 512a and 512b to control the on/off of the two laser sources 510a and 510b. In addition, the control computer 560 is also operably coupled to the microwave source 530 and the switch 532 to control the application of microwaves to the sample 520.

Methods of Automated Microscopy Using Encoded Markers

Figure 6A:
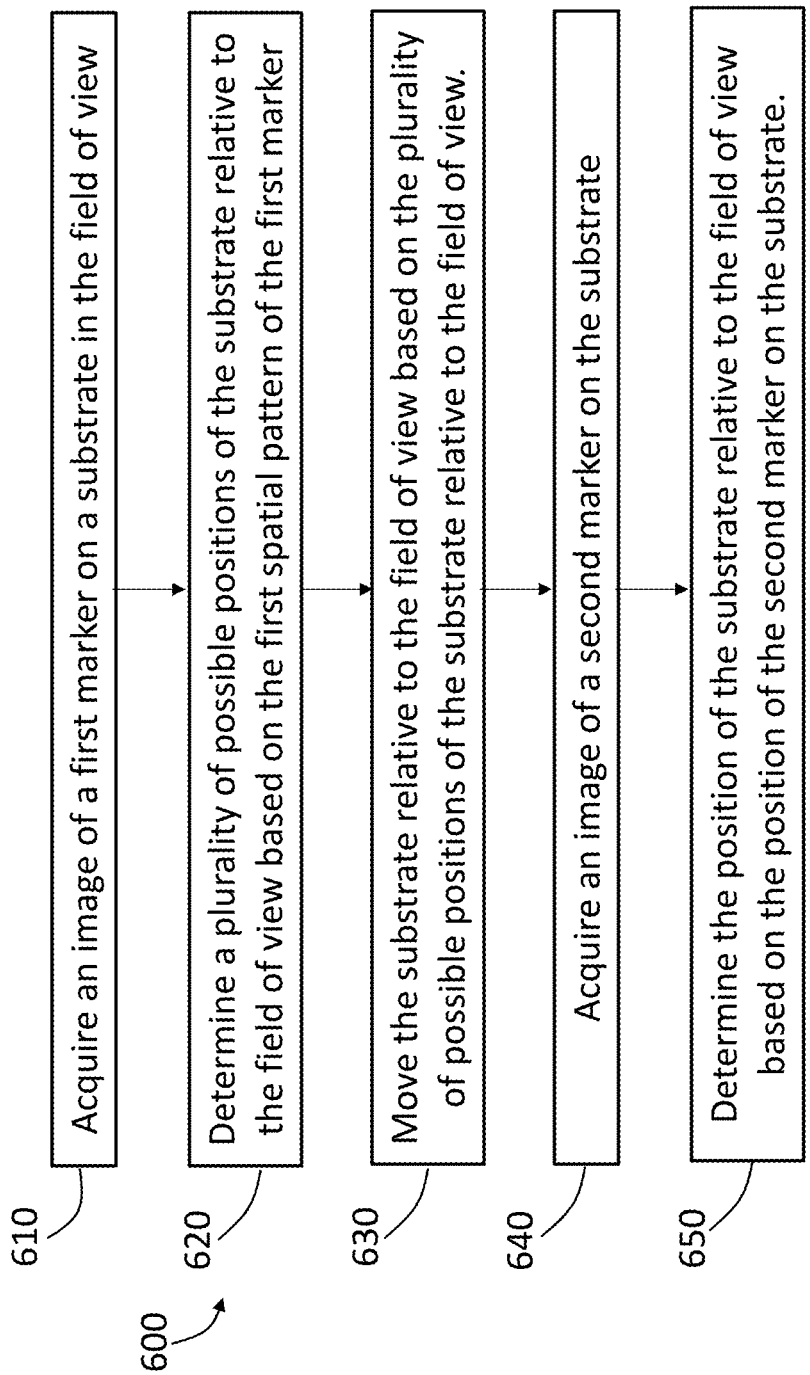
FIGS. 6A and 6B illustrate a method of automated microscopy using encoded markers.

FIG. 6A illustrates a method 600 of automated microscopy using encoded markers. The method 600 includes, at 610, acquiring an image of a first marker on a substrate in the field of view of an imaging system. The first marker has a first spatial pattern representing a position of the first marker relative to the substrate. At 620, a processor determines possible positions of the substrate relative to the field of view based on the first spatial pattern. In this instance, the first marker can be a non-unique marker. The method 600 also includes, at 630, moving the substrate relative to the field of view based on the possible positions of the substrate relative to the field of view. For example, the substrate may include a 2D array of markers having alternating rows of markers encoded with row information and column information, respectively. The first marker may include only the row number, in which case the substrate can be moved to the next row so as to acquire column information encoded in the markers in the adjacent row of markers.

At 640, the imaging system is used to acquire an image of a second marker on the substrate in the field of view. The second marker has a second pattern representing a position of the second marker relative to the substrate. Based on the positon of the second marker on the substrate, the position of the substrate relative to the field of view can be determined by the processor.

The first and second markers can be encoded with information other than the location information. For example, the markers can be encoded with a checksum, and determining the possible positions from the first (or second) marker can include decoding the checksum represented by the first spatial pattern and verifying at least one possible position based on the checksum.

In another example, the markers can include an error correction code, and determining the possible positions from the first (or second) marker includes decoding the error correction code represented by the first (or second) spatial pattern and recovering the position of the first (or second) marker relative to the substrate encoded in the first (or second) spatial pattern based on the error correction code. In yet another example, the markers are encoded with a version number, and determining the possible positions from the first (or second) marker includes identifying the version of the substrate based on the first (or second) spatial pattern.

At 630, a translation stage can be used to move the substrate relative to the field of the view along a lateral direction. Alternatively or additionally, the translation stage (or a separate motor) can move the substrate relative to the field of view along a vertical direction so as to change the focus of the imaging system and acquire a sharp image of the first marker and/or the second marker.

The first marker and the second marker can be fabricated on the substrate with techniques such as electron beam lithography such that the precision of their locations can be on the order of 50 nm or finer (e.g., about 50 nm, about 40 nm, about 30 nm, about 20 nm, or finer, including any values and sub ranges in between). In this instance, the translation stage can move the substrate (or the imaging system) at a first level of precision, and the position of the substrate determined by the processor can have a second level of precision finer than the first level of precision. Similarly, the imaging system can have a diffraction limit, and the first level of precision can be finer than the diffraction limit. Accordingly, the precision of the positon determined by the method 600 can be independent of the translation stage and the imaging system, thereby allowing significant flexibility in configuring the hardware.

The processor can also be configured to determine a direction of motion for the translation stage based on the first marker and/or the second marker. For example, the processor can be configured to estimate distances between respective possible positions associated with the first marker and the second position, and then select the direction of motion based on the distances from the respective possible positions to the second position. In another example, the processor can select the direction of motion based on an expected information content available from the image of the second marker.

Figure 6B:
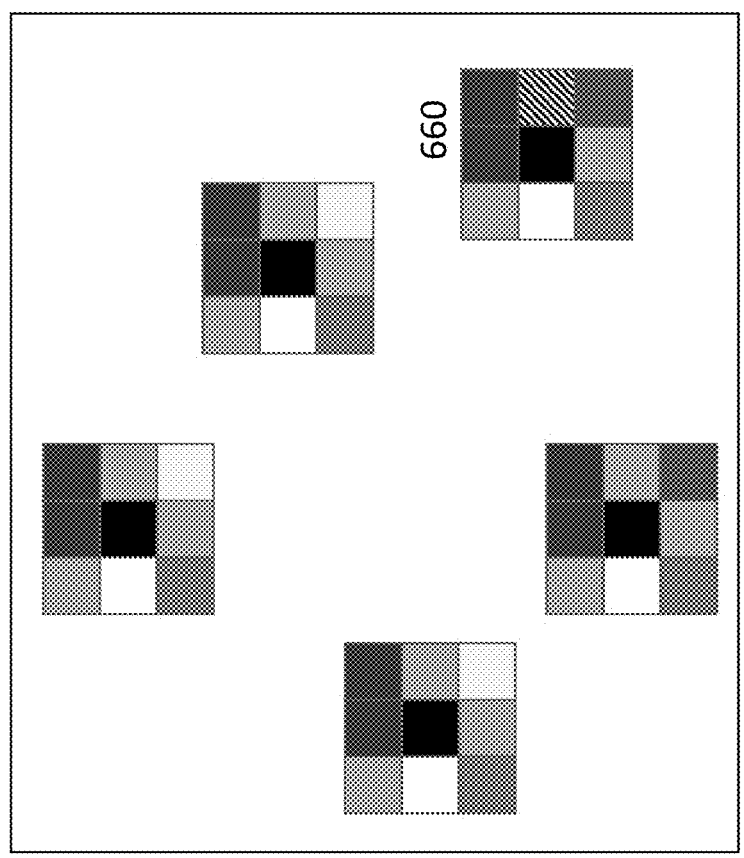

FIG. 6B illustrates the selection of movement direction based on the expected information content available from the image of the second marker. The goal of this step is to decrease the number of possible positions with the next move. To this end, the user can choose a direction that has the most information. As illustrated in FIG. 6B, out of the several possible positions (central blocks), the position 660 (on the lower right corner) has one unique position (i.e. highest information content) nearby. Accordingly, this position 660 can be used to determine as the direction of motion.

The method 600 described herein can be configured/adapted for localization and/or navigation. During localization, the instrument of interest (e.g., the imaging system) makes observations of the surrounding environment, such as the current field of view. The observations are compared to a known world (e.g., stored in a database), and a list of possible locations of the instrument is determined based on the comparison. The instrument then moves around the sample. The movements are recorded and a certain amount of error is taken into account due to imperfect execution of instrument instructions. The amount of error generated by the instrument is learned over time, resulting in more accurate belief updates in future tasks. Over time, after enough observations have been made, the system is able to accurately determine the location of the instrument.

In one example, a single observation can provide sufficient information to determine the location of the instrument (i.e., in the case of perfect information). For example, the sample can be patterned with unique markers and each marker can be used to determine the current location of the instrument.

In another example, the method 600 is employed in environments with incomplete and potentially incorrect information. These environments may include cases where non-unique markers are used, the markers are fabricated with imperfections, and/or the measurements are corrupted by noise. In environments with incomplete information, a single observation usually provides partial information regarding the instrument's location. The partial information allows the system to narrow down the number of potential locations significantly, but not entirely. After several observations, with error taken into account, the localization system is then able to accurately determine the correct location using Monte Carlo Localization (MCL).

Similarly, in environments with potentially incorrect information, or when using instruments that result in potentially incorrect observations (see, e.g. FIGS. 7A-7C), the localization system is still able to converge to a correct location. The MCL process assumes some amount of incorrect information/observations, and in doing so ensures that no single observation can significantly modify the belief (due to the probabilistic nature of the MCL process).

During navigation, the system is provided with a goal position (also referred to as a target position) and the task of navigation is to move the instrument towards the goal position. Based on the current belief of the localization system, a process or determines two possible courses of actions. The first course of action is to instruct the instrument to move in a manner that can allow the localization system to more efficiently (e.g., more quickly) determine the instrument's location. In other words, the instrument can move in the direction of largest expected information gain. For example, the processor can simulate the next series of motions (without performing them) while keeping track of every possible outcome of every possible choice (i.e. basically a breadth-first search of a decision tree). The calculation can be terminated either after evaluating every possible series of moves left. Alternatively, the calculation can be terminated when the result is satisfactory. Even though the next move may be potentially non-perfect in this instance, even one level of the decision tree can result in quite a good choice. This course of action can be taken when, for example, there is low confidence in the system's current belief and acquiring more accurate information about the current location of the instrument can be helpful in taking the next movement toward the goal position.

The second course of action is to instruct the instrument to move towards the goal position. This course of action can be taken when, for example, there is high confidence in the system's current belief.

As the confidence in the belief of the localization system increases, so does the accuracy of the navigation system. For example, if no information is known about where the instrument is located, the direction taken by the instrument is uninformed and likely to be not in the direction towards the goal position. As the system becomes more and more confident of the instruments location, the expected direction to the goal, as weighted by the instrument's belief, becomes more and more accurate. This can result in the instrument moving in a seemingly random direction for the first few steps. After learning the current location with more accuracy, the instrument moves in roughly the right and straight direction towards the goal position.

FIGS. 7A-7D show motion traces of an instrument toward a goal position with 3 bits, 4 bits, 6 bits, and an infinite (perfectly unique) number of bits represented by the markers. The instrument (e.g., a microscope) is initially placed on the left part of the images, and the line shows the course it takes to reach a target position on the right. The dots can be interpreted as a metric to the confidence of the microscope's position. As can be seen from FIGS. 7A-7D, increasing the number of bits encoded in the markers allows the microscope to more efficiently and quickly move toward the goal position.

Fabrication of Nanophotonic Devices Using Automated Microscopy

FIGS. 8A-8F illustrate a method 800 of fabricating nanophotonic devices using the automated microscopy techniques described above. There is currently an increasingly significant interest in patterning nano-photonic devices around fluorescent defect centers in diamond to collect and guide quantum light on a chip. At least three approaches can be used for the fabrication. The first approach includes patterning an array of devices regardless of the position of the emitters. This approach is straightforward and easy to implement. However, since the emitters are randomly distributed across the chip, the resulting yield can be very low, i.e., only few devices are actually fabricated around any defect center. The second approach includes creating an array of devices first and then attempting to engineer the emitter in the devices. The limitation of this approach is the ability to deterministically position and create the emitters. This can be accomplished, but the process is usually very challenging. The third approach includes registering randomly positioned defect centers and positioning the devices around those registered sites.

The method 800 illustrated in FIGS. 8A-8F employs the third approach. In this method 800, a diamond substrate 810 is cleaned and the surface is patterned with a coordinate system (e.g., a square grid) formed by markers 820. The markers 820 can be fabricated using, for example, electron-beam lithography (EBL). Spherical-aberration grids can also be patterned towards the center of the substrate 810 to be employed for correcting aberrations introduced through the imaging system. Large crosses are also patterned at the four corners of the substrate 810 to re-align the coordinate system with the EBL machine. All of these structures are etched directly into the diamond surface to assure their permanence throughout cleaning and fabrication.

Figures 8A, 8B, 8C:
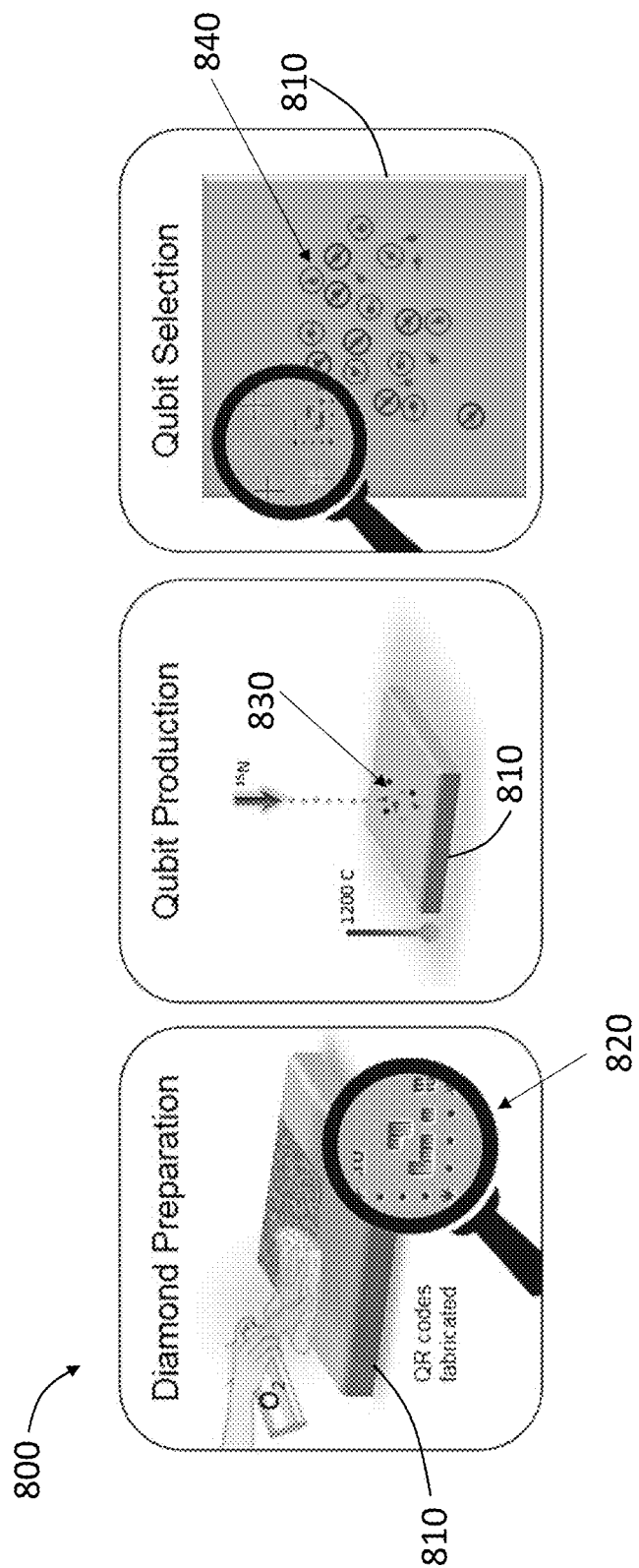

In FIG. 8B, defect centers 830 are introduced into the substrate 810 using ion implantation followed by annealing at a high temperature (e.g., about 1200° C.). In FIG. 8C, the defect centers 830 are located and characterized using the automated microscopy techniques described above. In this technique, the microscope can be equipped with two excitation sources (e.g., see FIG. 5). A 3 W 532 nm laser is used to excite the emitters across a full field of view (about 50 µm×50 µm). The imaging system can be optimized to collect light emitted by the emitters (e.g., at about 637 nm) and filter out the excitation light. A second red LED (at about 637 nm) can be used as a bright broadband source to image the markers 820 in the coordinate system etched into the diamond substrate 810. This particular LED can be used to avoid chromatic aberrations due to the imaging system.

After creating the coordinate system, the microscope can easily navigate the diamond substrate 810. At each position, white-light and fluorescent images are acquired. Microscope operation features ensure that the substrate 810 can be divided into fields-of-view that contain four markers with one at each corner. This allows the processor to calculate the pixel-coordinate system to the fitted global coordinate system with great accuracy. A Gaussian fit to every detected fluorescent spot allows the system to accurately localize each emitter (see, e.g., FIG. 10 below). As shown in FIG. 8C, identifiers 840 can be added to the defect centers 830 in the images displayed by the imaging system so as to facilitate subsequent processing.

In FIG. 8D, photonic structures 850 (e.g., cavities) to enhance light-matter interaction are patterned around localized centers 830 to form structure-defect nodes. At this step, the automated microscopy technique can be used to navigate the diamond substrate 810 so as to position the fabrication instrument at the registered defect centers 830. In one example, the fabrication of the photonic structures 850 can be performed each time a defect center is located. In another example, the microscope can locate and register all defect centers 830 and store the location information into a database. During the fabrication of the photonic structures 850, the microscope then position the fabrication instrument to each defect center 830 based on the stored location information.

In FIG. 8E, the structure-defect nodes are re-characterized. At this step, the automated microscopy technique can be used again to check whether each photonic structure 850 is indeed fabricated around a corresponding defect center 830. This step can also determine the quality of each structure-defect node based on, for example, the optical coupling efficiency between the photonic structure 850 and the corresponding defect center 830. In FIG. 8F, the structure-defect nodes having the highest quality can be selected and transferred to a new host chip (not shown).

Figure 9B:
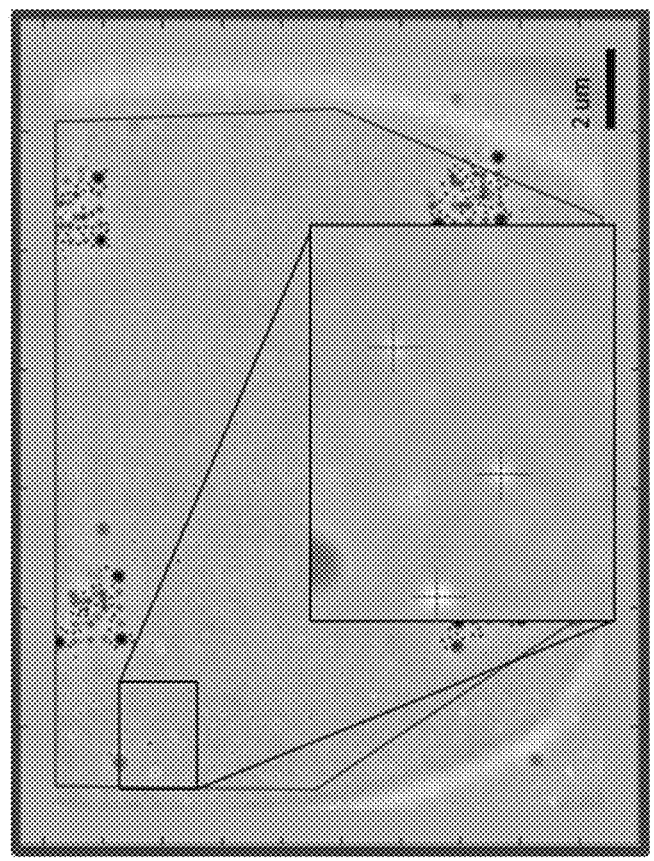
FIG. 9B shows a real-time image from the microscope as the microscope locates emitters on the chip shown in FIG. 9A.
Figure 9A:
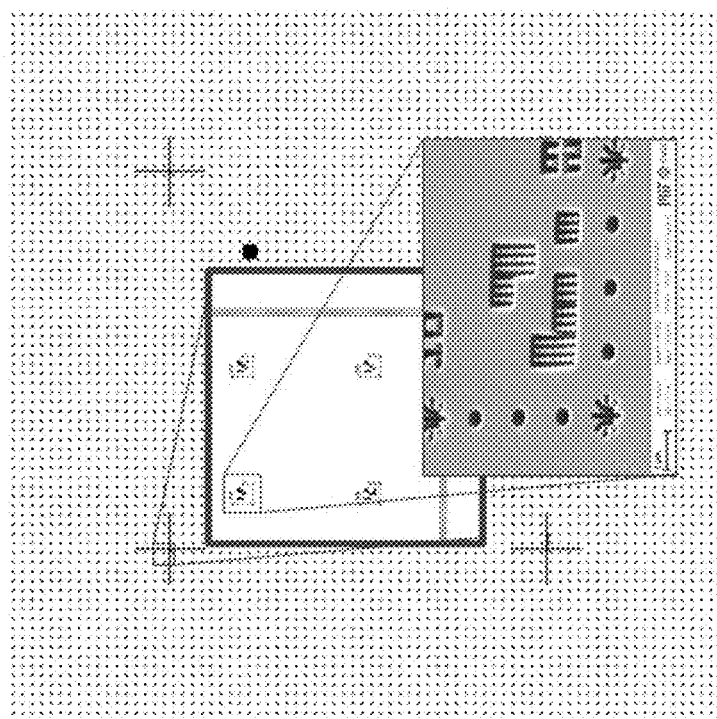
FIG. 9A shows an image of a full chip patterned with markers, electron beam lithography alignment markers, and spherical aberration correction grids.

FIG. 9A shows an image of a full chip patterned with markers, electron beam lithography alignment markers, and spherical aberration correction grids (e.g., produced in FIG. 8A). The last inset is a scanning electron microscopy (SEM) image of position marker. FIG. 9B shows a real-time image from the microscope as the microscope locates emitters (e.g., during the step illustrated in FIG. 8C). The border in FIG. 9B roughly maps to the scale of the border in FIG. 9A.

Figure 10:
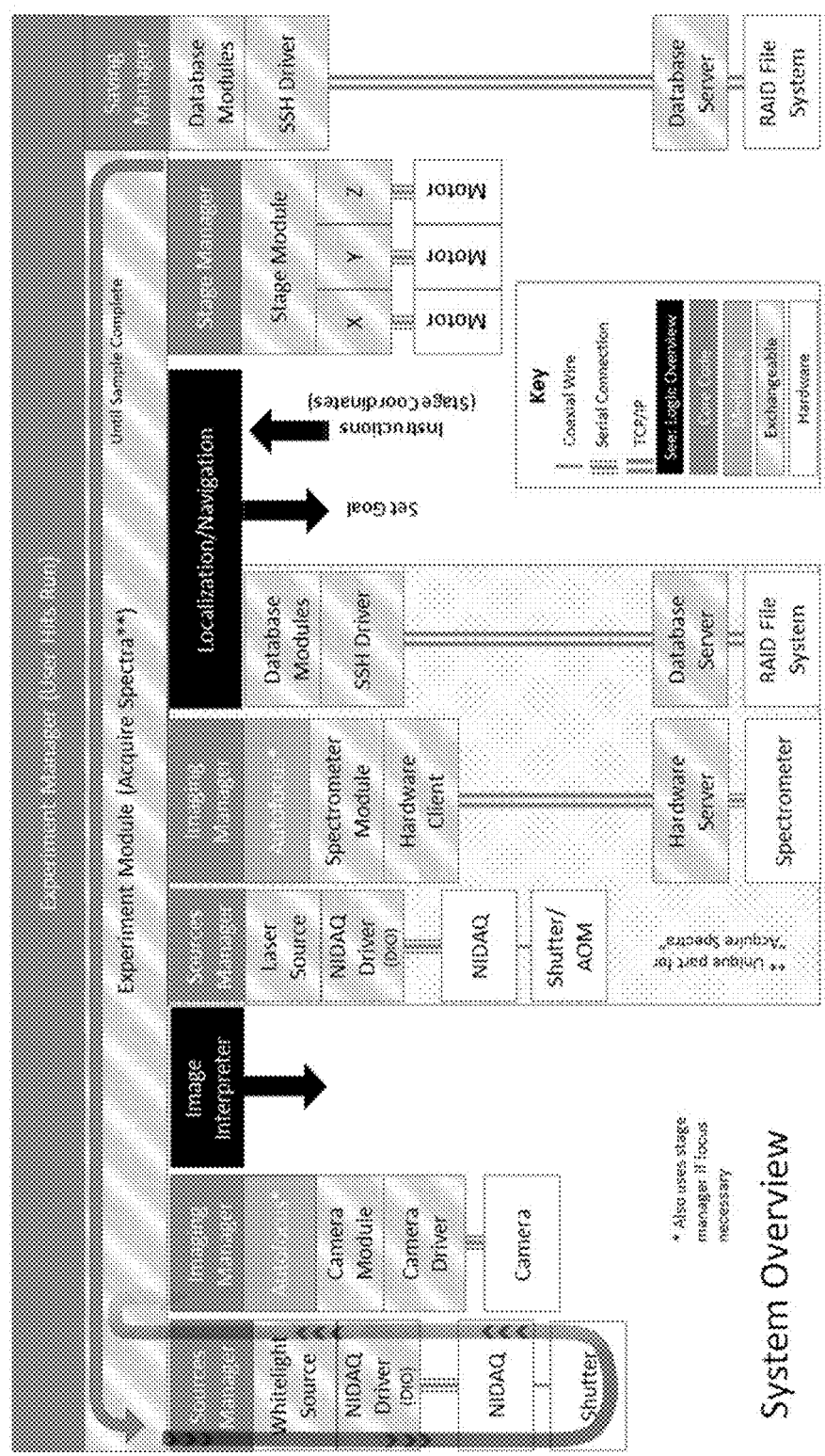
FIG. 10 shows a system overview for an example run of the method 800 illustrated in FIGS. 8A-8F.

FIG. 10 shows a system overview for an example run of the method 800 illustrated in FIGS. 8A-8F. Operations start on the left and go through stacks of modules (e.g., along the directions of the arrows) by descending into the stacks as the modules are called and ascending out as the modules return. The system navigates through a chip (e.g., the diamond substrate 810) and takes spectra as it runs.

The registered positions of the emitters are used to autonomously construct a fabrication file in which all the devices are aligned with emitters. The EBL machine operates to align its internal coordinate system to the diamond's coordinate system (indicated by the markers 820) by fitting the locations of the large crosses in the corners of the substrate 810. This alignment can be accomplished with accuracy on the order of nanometers (e.g., about 1 nm, about 2 nm, about 5 nm, about 10 nm, including any values and sub ranges in between).

As shown in FIG. 8E, the substrate 810 can be loaded into the autonomous microscope again to characterize the final device-emitter system (e.g., structure-defect nodes). This can be accomplished on another realization of the microscope that is integrated with a cryostat and galvanometers that are used to image using a confocal technique.

Figures 11A, 11B:
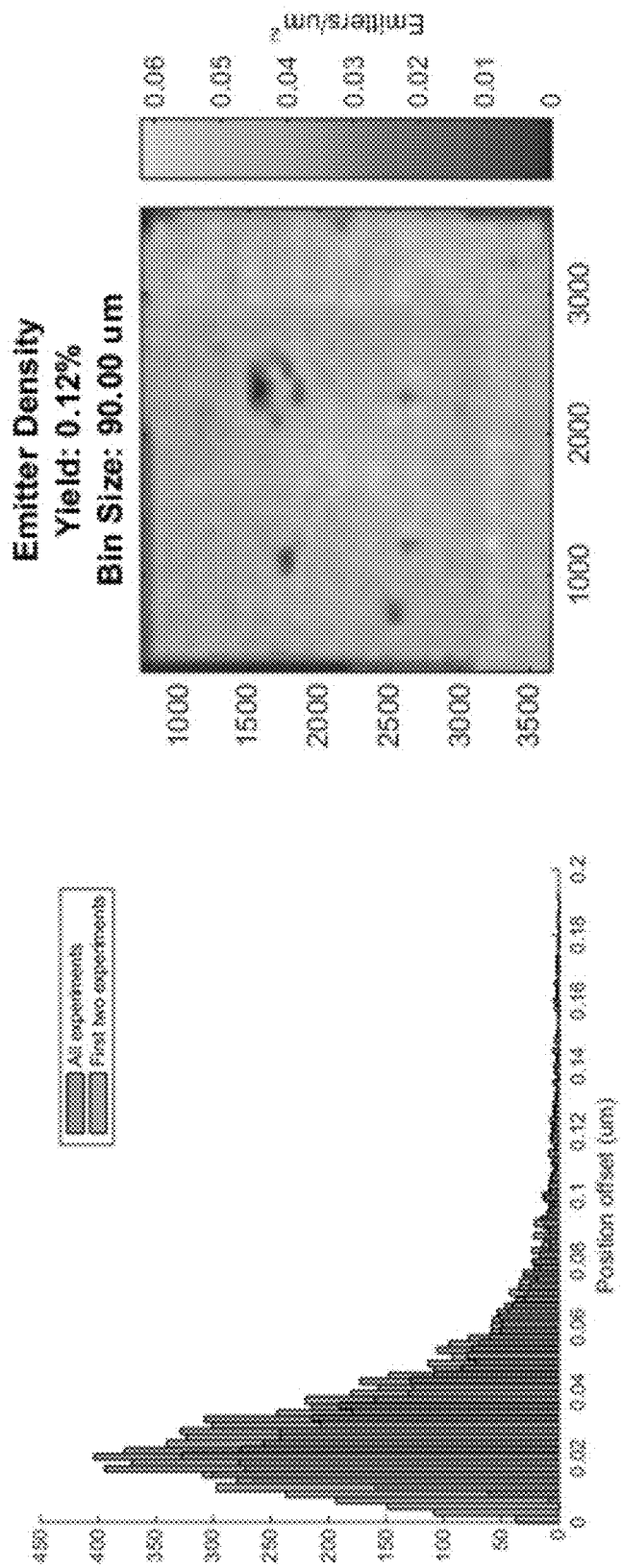
FIG. 11A shows the accuracy of the emitter detection achieved by the method illustrated in FIGS. 8A-8F.
FIG. 11B shows the density of the emitters across the macroscopic chip in the method illustrated in FIGS. 8A-8F.

FIG. 11A shows the accuracy of the emitter detection achieved by the methods 800. The data was gathered by repeating the localization across the entire chips many times, as the physical position of the sample changed between runs. This shows a localization precision of about 20 nm to about 30 nm. FIG. 11B shows the density of the emitters across the macroscopic chip 810. This is done by assigning emitters into bins of about 90 µm×90 µm.

Software Architecture to Implement Automatic Microscopy

Figure 12:
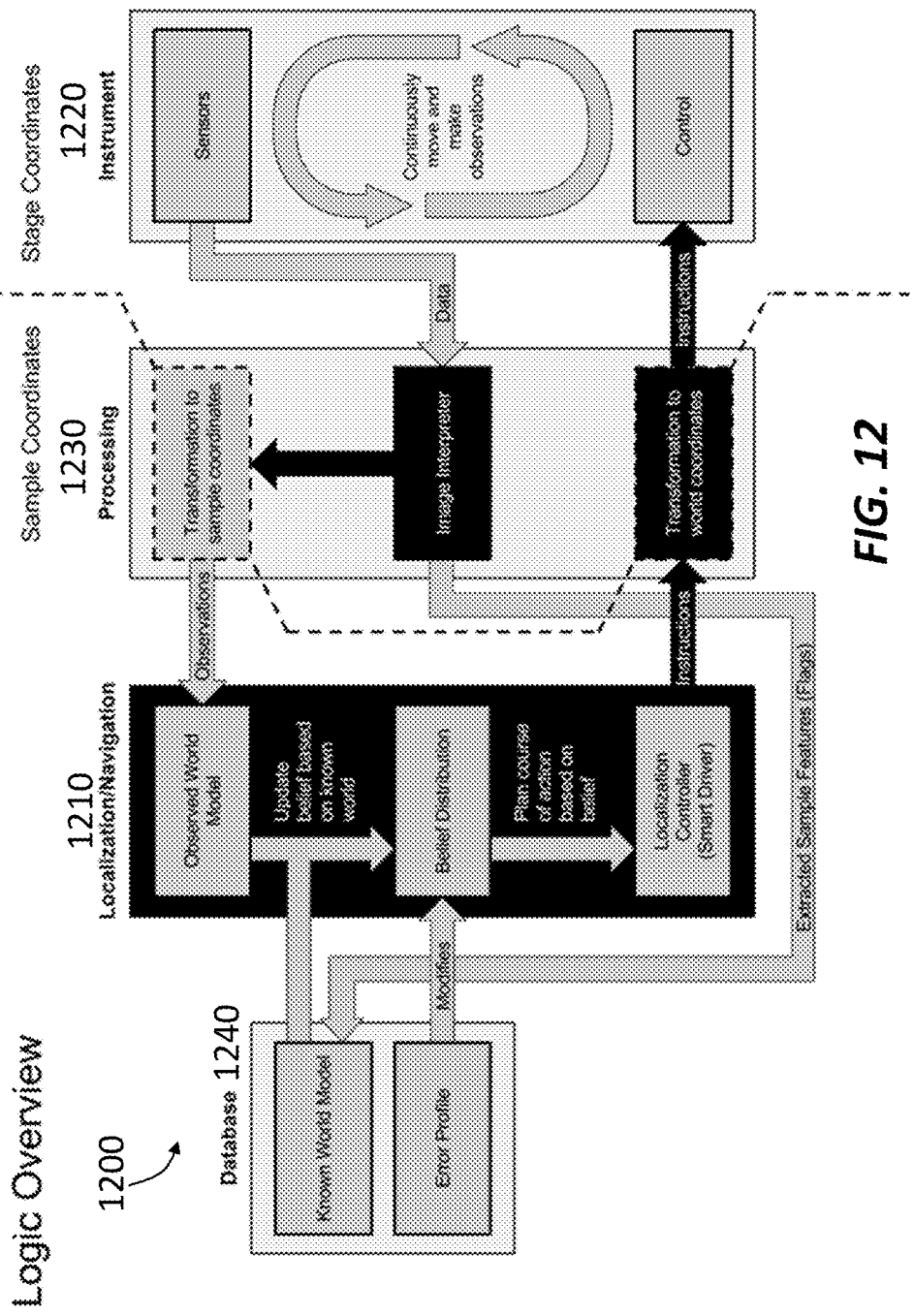
FIG. 12 shows a logical overview of a system to implement automatic microscopy.

FIG. 12 shows a logical overview of a system 1200 to implement automatic microscopy. A localization system 1210 takes observations from sensors in an instrument system 1220 as input. The observations are interpreted and transformed into sample coordinates by a processing system 1230. The localization system 1210 uses these processed observations to update the observed world model. Then, coupled with the known world model, the localization system 1210 generates a belief as to where the instrument may be located. This process uses Monte Carlo Localization (MCL) and takes into account the error profile of the instrument system 1220 as known or as learned over time.

Next, the localization system 1210 informs the navigation system (integrated with the localization system 1210) of its belief, which is used along with the goal position to determine a course of action. The course of action can include moving in the direction of maximum expected information gain in order to increase the accuracy of the belief, or moving in the expected direction of the goal position. This information of the course of action, after it has been transformed back into stage coordinates, is then served to the instrument controller upon request in order for the instrument system 1220 to execute the course of action. This process can repeat each time an observation is made by the instrument system 1220, which may be quite frequently or infrequently depending on the information density of the instrument's environment. Additionally, the interpreter of the sensor data may output sample features capable of being used in the future as part of the known world model. This means that the system is capable of learning more about the sample than it was originally given as the sample is explored.

The system 1200 also includes a non-volatile memory or database 1240 allowing users to instruct the software how to save data. There are at least two types of database modules: a manual database module and an automatic database module. An automatic database module is called after any image is taken, the experiment concludes, or it is signaled in a running experiment. The manual database modules allow simple manual save capability (e.g., built on of Matlab's file UI) to a rather complex networked database scheme. Additional metadata can be saved on top of user data, including imaging and experiment module properties and the current Git commit. This can provide an exact snapshot of the full code base upon saving.

Figure 13:
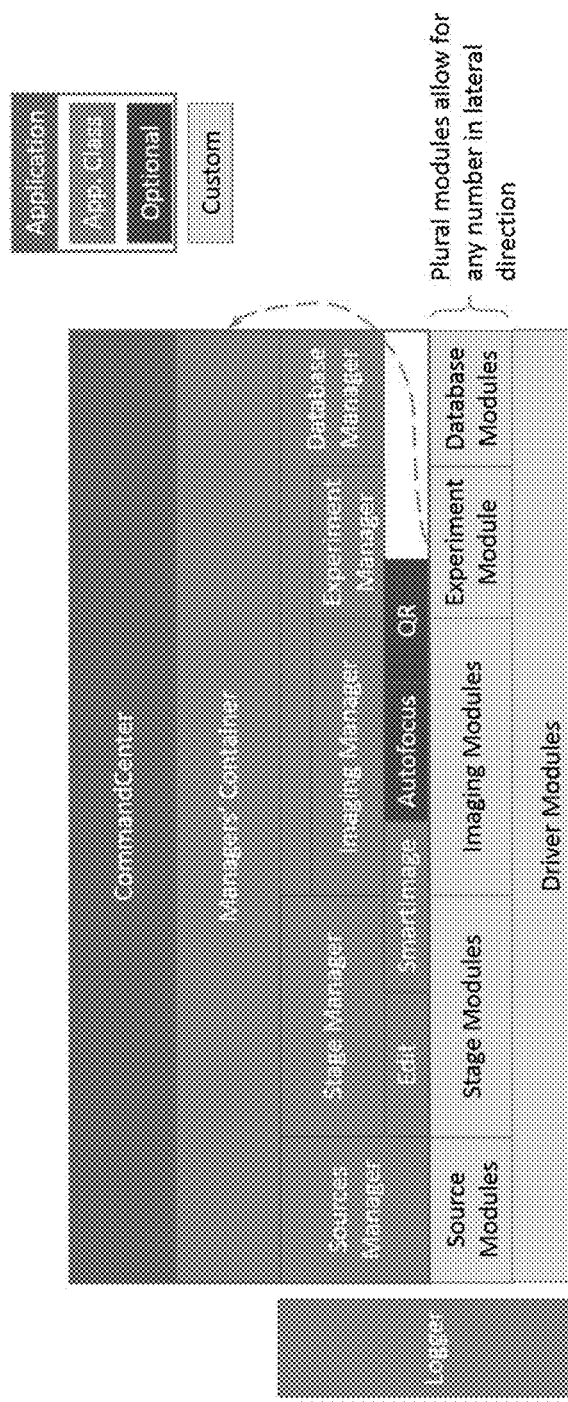
FIG. 13 shows a structure of command center code base to implement automated microscopy.

FIG. 13 shows a structure of command center code base to implement automated microscopy. The software can be segregated into two categories: core code and user code. The core code is primarily responsible for managing the user-interface, organizing active user modules, logging and managing uncaught errors. The user code, called modules, controls hardware and experimental flow.

When operating manually, the core code can operate in remote mode if desired. In this mode of operation, a version of the software is operating on a remote machine in server mode and listens on a specified port. A local version of the software can run in client mode. Instead of reacting to users' actions locally, the local version can encode the request and send the request to the server machine and wait for the result.

Every object represented in FIG. 13 can be instantiated as a Matlab class. Class handles for the managers are provided for most user methods to give the user true control from the level of abstraction that they are comfortable working in. Modules can inherit a special "singleton" class, which ensures that each instance of a particular module is instantiated only once. This can be helpful in the equipment control domain because it can prevent two modules from potential confusion regarding the current state of the equipment. It can also simplify the process of grabbing a handle to a desired module without the need to track the potential use in other modules. The managers create and destroy modules at the request of the user or a currently running module.

Figure 14:
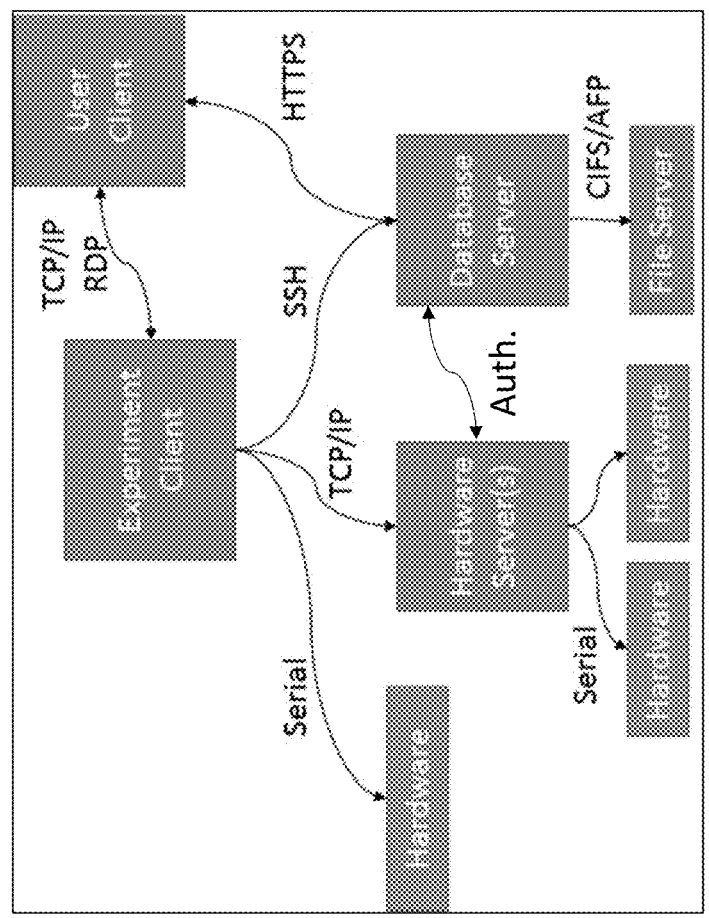
FIG. 14 shows a service layout to implement automated microscopy including distributed set of resources controlled by server/client models implemented in Python.

FIG. 14 shows a service layout including distributed set of resources controlled by server/client models implemented in Python. In practice, equipment to carry out an application may be located on the same computer or on a different computer. For example, the equipment may be shared, or an additional motherboard may be used. As such, Python-based client/server models are provided to interface with hardware using DLLs or COM ports, as illustrated in FIG. 14. The Python client connects, using an SSL or SSH-based layer, to the server allowing traffic to be authenticated and secure. If the hardware control is sufficiently simple (e.g., calling DLL functions or sending direct commands over the COM port), the configuration can be taken care of in a configuration file. If it is too complicated, a user can also choose to write a Python class to handle the requests directly, such as a condition involving more advanced request parsing and/or client authentication (possibly via the database).

With the architecture illustrated in FIGS. 12-14, there can be at least two setups in which the software is implemented. Both systems share a networked database allowing a seamless use of each. A SQLite database can be configured on the network using a Python interface. A Secure Sockets Layer (SSL) protected web server (e.g., a Django backend with an Apache serve and a Foundation frontend) allows editing and viewing the database for authenticated users. A Secure Shell (SSH) interface enables the autonomous setups to securely interface with the database in an authenticated manner using registered asymmetric keys. The database can be customized through the web-interface to index any data-types, all of which can be linked to coordinates defined by the markers on the sample.

The first of the two microscopes can be configured to allow quick, room-temperature registration of emitters with some basic room temperature profiling. The second microscope can be equipped with a cryostat, allowing measurements at around 4 K. The low temperature allows a wider variety of measurements that can include resonant spectroscopy.

An experiment typically involves many processing and characterization steps, such as lithography (e.g., electron beam and optical patterning, metal layers, etc.), scanning electron micrograph (SEM) characterization, optical microscope characterization, elemental analysis (e.g., energy-dispersive X-ray spectroscopy or EDX), and magnetic field measurements. All of these steps can be linked to the same marker-defined coordinate system on the sample. Sample data can be stored in the cloud. In this manner, each sample produces many data layers that can be analyzed on a computer or directly on an instrument connected to the cloud. This allows systematic acquisition of data and characterization of samples.

Applications of Automated Microscopy

The automated microscopy technique described herein can be used in a wide range of applications. One example application is for fabrication of photonic structures around defect centers in a diamond chip, as illustrated in FIGS. 8A-8F. In another example, the technique can be used in biological research to trace samples (e.g., tumor cells) through processing and characterization steps. In yet another example, the technique can be used in biological screening to screen large samples including areas of interest for further study. The automatic microscopy can locate each area of interest and register their locations. Subsequent studies can be precisely guided by the registered locations. In yet another example, the technique can be used in medical screening to quickly navigate samples to detect certain features (e.g., an infection or tumorous cell). Similarly, the locations of the detected features can be registered for subsequence revisit.

In yet another example, the automated microscopy can be used to fabricate waveguides, cantilevers, 1D cavities, 2D cavities, and atomic force microscope (AFM) tips at desired locations. These locations can be determined and registered into a database. In addition, the automated microscopy can also be used in microchip validation/verification processes to ensure that chips are produced correctly and are not untampered with during shipment.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of locating a substrate within a field of view of an imaging system, the method comprising:
   acquiring, with the imaging system, an image of a first marker on the substrate in the field of view, the first marker having a first spatial pattern encoding a position of the first marker relative to the substrate according to a predetermined code;
   determining a plurality of possible positions of the substrate relative to the field of view based on the first spatial pattern;
   moving the substrate relative to the field of view based on the plurality of possible positions of the substrate relative to the field of view;
   acquiring, with the imaging system, an image of a second marker on the substrate in the field of view, the second marker having a second pattern encoding a position of the second marker relative to the substrate according to the predetermined code; and
   determining the position of the substrate relative to the field of view based on the position of the second marker on the substrate, wherein determining the plurality of possible positions comprises:
   decoding a checksum encoded by the first spatial pattern; and verifying at least one possible position in the plurality of possible positions based on the checksum.

2. The method of claim 1, wherein determining the plurality of possible positions comprises:
identifying a version of the substrate based on the first spatial pattern.

3. The method of claim 1, wherein moving the substrate relative to the field of view comprises moving the substrate laterally with a translation stage.

4. The method of claim 1, wherein moving the substrate relative to the field of view comprises changing a focus of the imaging system.

5. The method of claim 1, wherein:
moving the substrate comprises moving the substrate with a first level of precision; and
determining the position of the substrate comprises determining the position of the substrate with a second level of precision finer than the first level of precision.

6. The method of claim 1, wherein moving the substrate relative to the field of view comprises selecting a direction of motion based on the plurality of possible positions of the substrate relative to the field of view.

7. The method of claim 6, wherein selecting the direction of motion comprises:
estimating distances from respective possible positions in the plurality of possible positions to the position of the second marker on the substrate; and
selecting the direction of motion based on the distances from the respective possible positions to the position of the second marker on the substrate.

8. The method of claim 1, wherein moving the substrate relative to the field of view comprises selecting a direction of motion based on an expected information content available from the image of the second marker.

9. The method of claim 1, further comprising:
compensating for aberration in the image of the second marker based on the second spatial pattern.

10. The method of claim 1, further comprising:
moving the substrate to a third position relative to the field of view based on the position of the second marker on the substrate.

11. An imaging system comprising:
an image sensor to acquire an image of a first marker on a substrate in the field of view, the first marker having a first spatial pattern encoding a position of the first marker relative to the substrate according to a predetermined code;
a processor, operably coupled to the image sensor, to determine at least one possible position of the substrate relative to the field of view based on the first spatial pattern; and
a translation stage, operably coupled to the processor, to move the substrate relative to the field of view based on the at least one possible position of the substrate relative to the field of view,
wherein the processor is configured to decode a checksum encoded by the first spatial pattern and to verify the at least one possible position based on the checksum.

12. The imaging system of claim 11, wherein:
the imaging system is configured to acquire an image of a second marker on a substrate in the field of view, the second marker having a second pattern encoding a position of the second marker relative to the substrate according to the predetermined code; and
the processor is configured to determine the position of the substrate relative to the field of view based on the position of the second marker on the substrate.

13. The imaging system of claim 12, wherein the translation stage is configured to move the substrate to a third position relative to the field of view based on the position of the second marker on the substrate.

14. The imaging system of claim 12, wherein the processor is configured to select a direction of motion to the position of the second marker on the substrate based on the at least one possible position of the substrate relative to the field of view.

15. The imaging system of claim 14, wherein the at least one possible position comprises a plurality of possible positions and the processor is configured to select the direction of motion by:
estimating distances from respective possible positions in the plurality of possible positions to the position of the second marker on the substrate; and
selecting the direction of motion based on the distances from the respective possible positions to the position of the second marker on the substrate.

16. The imaging system of claim 11, wherein the processor is configured to identify a version of the substrate based on the first spatial pattern.

17. The imaging system of claim 11, wherein:
the translation stage is configured to move the substrate with a first level of precision; and
the processor is configured to determine the at least one position with a second level of precision finer than the first level of precision.

18. The imaging system of claim 11, wherein the processor is configured to compensate for aberration in the image of the first marker based on the first spatial pattern.

19. A method of locating a substrate within a field of view of an imaging system, the method comprising:
acquiring, with the imaging system, an image of a first marker on the substrate in the field of view, the first marker having a first unique spatial pattern encoding a position of the first marker relative to the substrate and a checksum;
determining at least one possible position of the substrate relative to the field of view based on the position of the first marker relative to the substrate and the checksum; and
moving the substrate relative to the field of view to a target position based on the at least one possible position of the substrate relative to the field of view.

20. The method of claim 19, further comprising:
acquiring, with the imaging system, an image of an emitter on the substrate at the target position.

21. The method of claim 20, further comprising:
registering a position of the emitter relative to the substrate.

22. The method of claim 20, further comprising:
fabricating a nanophotonic device comprising the emitter on the substrate.

23. A method of locating a substrate within a field of view of an imaging system, the method comprising:
acquiring, with the imaging system, an image of a first marker on the substrate in the field of view, the first marker having a first spatial pattern encoding a position of the first marker relative to the substrate according to a predetermined code;
determining a plurality of possible positions of the substrate relative to the field of view based on the first spatial pattern;
moving the substrate relative to the field of view based on the plurality of possible positions of the substrate relative to the field of view;

acquiring, with the imaging system, an image of a second marker on the substrate in the field of view, the second marker having a second pattern encoding a position of the second marker relative to the substrate according to the predetermined code; and determining the position of the substrate relative to the field of view based on the position of the second marker on the substrate, wherein determining the plurality of possible positions comprises:

decoding an error correction code encoded by the first spatial pattern; and recovering the position of the first marker relative to the substrate encoded in the first spatial pattern based on the error correction code.

24. A method of locating a substrate within a field of view of an imaging system, the method comprising:

acquiring, with the imaging system, an image of a first marker on the substrate in the field of view, the first marker having a first spatial pattern encoding a position of the first marker relative to the substrate according to a predetermined code;

determining a plurality of possible positions of the substrate relative to the field of view based on the first spatial pattern;

moving the substrate relative to the field of view based on the plurality of possible positions of the substrate relative to the field of view;

acquiring, with the imaging system, an image of a second marker on the substrate in the field of view, the second marker having a second pattern encoding a position of the second marker relative to the substrate according to the predetermined code; and determining the position of the substrate relative to the field of view based on the position of the second marker on the substrate, wherein determining the position of the substrate comprises determining the position with a resolution finer than a diffraction limit of the imaging system.

25. An imaging system comprising:

an image sensor to acquire an image of a first marker on a substrate in the field of view, the first marker having a first spatial pattern encoding a position of the first marker relative to the substrate according to a predetermined code;

a processor, operably coupled to the image sensor, to determine at least one possible position of the substrate relative to the field of view based on the first spatial pattern; and a translation stage, operably coupled to the processor, to move the substrate relative to the field of view based on the at least one possible position of the substrate relative to the field of view, wherein the processor is configured to decode an error correction code encoded by the first spatial pattern and to recover the at least one possible position of the first marker relative to the substrate encoded in the first spatial pattern based on the error correction code.

26. An imaging system comprising:

an image sensor to acquire an image of a first marker on a substrate in the field of view, the first marker having a first spatial pattern encoding a position of the first marker relative to the substrate according to a predetermined code;

a processor, operably coupled to the image sensor, to determine at least one possible position of the substrate relative to the field of view based on the first spatial pattern; and a translation stage, operably coupled to the processor, to move the substrate relative to the field of view based on the at least one possible position of the substrate relative to the field of view, wherein the processor is configured to determine the position of the substrate with a resolution finer than a diffraction limit of the imaging system.

* * * * *